(12) United States Patent
Härter et al.

(10) Patent No.: US 6,649,618 B2
(45) Date of Patent: Nov. 18, 2003

(54) SUBSTITUTED AMIDOALKYL-URACILS AND THEIR USE

(75) Inventors: Michael Härter, Leverkusen (DE); Barbara Albrecht, Wuppertal (DE); Michael Gerisch, Wuppertal (DE); Gabriele Handke, Wülfrath (DE); Joachim Hütter, Wuppertal (DE); Axel Jensen, Velbert (DE); Thomas Krahn, Hagen (DE); Joachim Mittendorf, Wuppertal (DE); Felix Oehme, Wuppertal (DE); Karl-Heinz Schlemmer, Wuppertal (DE); Henning Steinhagen, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/906,296

(22) Filed: Jul. 16, 2001

(65) Prior Publication Data

US 2003/0022905 A1 Jan. 30, 2003

(30) Foreign Application Priority Data

Jul. 18, 2000 (DE) ......................................... 100 34 801

(51) Int. Cl.[7] ................ C07D 491/048; C07D 491/052; C07D 495/04; A61K 31/517; A61K 31/519
(52) U.S. Cl. ..................... 514/258.1; 544/253; 544/278; 514/260.1
(58) Field of Search ................................. 544/253, 278; 514/260.1, 258.1

(56) References Cited

FOREIGN PATENT DOCUMENTS

| DE | 1959705 | 3/1971 |
|----|---------|--------|
| DE | 2126148 | 7/1972 |
| DE | 2142317 | 1/1973 |
| JP | 3264579 | 11/1991 |
| WO | 9833802 | 6/1998 |
| WO | 0042025 | 7/2000 |

OTHER PUBLICATIONS

Chaby (Drug Discovery Today 4(5) 209–221, May 1999).*
Opal et al (Infectious Disease Clinics of North America 13(2), pp. 285–297, Jun. 1999).*
Patent Abstracts of Japan, vol. 016, No. 071 (C–0913), Feb. 21, 1992, JP 03 264579.
Golankiewicz, K., and Celewics, L., "Synthesis of New Derivatives of 1,1'–Trimethylenebispyrimidines", P Journal of Chemistry, 52(5): 1035–1038 (1978).
Basnak, I., Balkan, A., Coe, P. L., and Walker, R. T., "The Synthesis of Some 5–Substituted and 5,6–Disubstituted 2'–Deoxyuridines", Nucleosides & Nucleotides, 13(1–3): 177–196 (1994).

Cuzzocrea, S., Zingarelli, B., Gilad, E., Hake, P., Salzman, A. L., Szabo, C., "Protective effects of 3–aminobenzamide, and inhibitor of poly (ADP–ribose) synthase in a carrageenan–induced model of local inflammation", European Journal of Pharmacology, 342: 67–76 (1998).
Draminski, M., Frass, E., "Alkylated Derivatives of Uracil. Part IX. Synthesis of N–(2,3–Dihydroxypropyl) Derivatives of 5,6–Tetramethyleneuracil, Structural Analogs of Nucleosides", Polish Journal of Chemistry, 55: 1547–1552 (1981).
Endres, M., Wang, Z.–Q., Namura, S., Waeber, C., Moskowitz, M., "Ischemic Brain Injury is Mediated by the Activation of Poly(ADP–Ribose)Polymerase", Journal of Cerebral Blood Flow and Metabolism, 17: 1143–1151 (1997).
Eriksson, C., Busk, L., Brittebo, E. B., "3–Aminobenzamide: Effects on Cytochrome P450–Dependent Metabolism of Chemicals and on the Toxicity of Dichlobenil in the Olfactory Mucosa", Toxicology and Applied Pharmacology, 136: 324–331 (1996).
Jijon, H. B., Churchill, T., Malfair, D., Wessler, A., Jewell, L. D., Parsons, H. G., Madsen, K. L., "Inhibition of poly-(ADP–ribose) polymerase attenuates inflammation in a model of chronic colitis", Am. J. Physiol. Gastrointest. Liver Physiol. 279: G641–G651 (2000).
Peczak, G., Draminski, M., "Alkylated Derivatives of Uracil. Part X. Synthesis of 2,4–Diketo–5,6,7,8–Tetrahydroquinazoline", Polish Journal of Chemistry, 59: 317–326 (1985).
Rahim, S. G., Trivedi, N., Bogunovic–Batchelor, M. V., Hardy, G. W., Mills, G., Selway, J. W. T., Snowden, W., Littler, E., Coe, P. L., Basnak, I., Whale, R. F., Walker, R. T., "Synthesis and Anti–Herpes Virus Activity of 2'–Deoxy-4'–thiopyridimidine Nucleosides", J. Med. Chem., 39: 789–795 (1996).

(List continued on next page.)

*Primary Examiner*—Mark L. Berch
*Assistant Examiner*—Kahsay Habte

(57) ABSTRACT

Novel amidoalkyl-uracil derivatives of the formula (I)

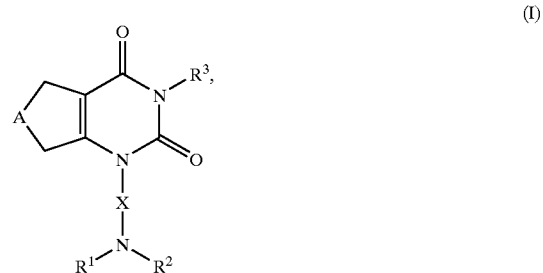

in which A represents 1–3 ring atoms and X represents optionally substituted $(C_2-C_{10})$alkylene or $(C_3-C_8)$ cycloalkylene as defined in claim 1, a process for their preparation, and their use as medicaments for the prophylaxis and/or treatment of disorders are described.

11 Claims, No Drawings

OTHER PUBLICATIONS

Renault, J., Laduree, D., Robba, M., "Synthesis and Antiviral Study of Cyclopentano [d] Pyrimdine–2,4–Diones and Octahydroquinazoline–2,4–Diones Acyclic Nucleotides as Potential Anti–HIV Agents", Nucleosides & Nucleosides, 13(4): 891–901 (1994).

Shimabukuro, M., Ohneda, M., Lee, Y., Unger, R. H., "Role of Nitric Oxide in Obesity–Induced β Cell Disease", Journal of Clinical Investigation, 100(2): 290–295 (1997).

Szabo, C., Dawson, V., "Role of poly(ADP–ribose) synthetase in inflammation and ischaemia–reperfusion", TIPS, 19: 287–298 (Jul. 1998).

Szabo, C., Cussocrea, S., Hake, P., Scott, G. S., Hirsch, R., Salzman, A. L., "Protective Effect of an Inhibitor of Poly-(ADP–Ribose) Synthetase in Collagen–Induced Arthritis", Japanese J. Pharm., 75, Supp. I:102, P317 (1997).

Tabuchi, K., Tsuji, S., Hara, A., Ito, Z., Serizawa, F., Nakagawa, A., Kusakari, J., "Poly(Adenosine Diphosphate–Ribose) Synthetase Inhibitor 3–Aminobenzamide Alleviates Cochlear Dysfunction Induced by Transient Ischemia", Ann Otol Rhinol Laryngol, 110(2): 118–121 (2001).

Thiemermann, C., Bowes, J., Myint, F. P., Vane, J. R., "Inhibition of the activity of poly(ADP ribose) synthetase reduces ischemia–reperfusion injury in the heart and skeletal muscle", Proc. Natl. Acad. Sci. USA, 94: 679–683 (Jan. 1997).

Vromen, A., Arkovitz, M. S., Zingarelli, B., Salzman, A. L., Garcia, V. G., Szabo, C., "Low–Level Expression and Limited Role for the Inducible Isoform of Nitric Oxide Synthase in the Vascular Hyporeactivity and Mortality Associated with Cecal Ligation and Puncture in the Rat", SHOCK, 6(4): 248–253 (1996).

Wallis, R. A., Panizzon, K. L., Girard, J. M., "Traumatic Neuroprotection with Inhibitors of Nitric Oxide and ADP–Ribosylation", Brain Research, 710: 169–177 (1996).

Wallis, R. A., Panizzon, K. L., Henry, D., Wasterlain, C. G., "Neuroprotection against nitric oxide injury with inhibitors of ADP–ribosylation", NeuroReport, 5(3): 245–248 (1993).

Watanabe, Y., Usui, H., Shibano, T., Tanaka, T., Kanao, M., "Syntheses of Monocyclic and Bicyclic 2,4(1H,3H)–Pyrimidinediones and Their Serotonin 2 Antagonist Activities", Chem. Pharm. Bull., 38(10): 2726–2732 (1990).

Weltin, D., Marchal, J., Dufour, P., Potworowski, E., Oth, D., Bischoff, P., Effect of 6(5H)–phenanthridinone, an Inhibitor ofPoly(ADP–ribose) Polymerase, on Cultured Tumor Cells, Oncology Research, 6(9): 399–403 (1994).

Zhang, J., Dawson, V. L., Dawson, T. M., Snyder, S. H., "Nitric Oxide Activation of Poly(ADP–Ribose) Synthetase in Neurotoxicity", Science, 263: 687–689 (1994).

* cited by examiner

SUBSTITUTED AMIDOALKYL-URACILS AND THEIR USE

The present invention relates to novel chemical compounds, to a process for their preparation and to their use as medicaments, in particular for the prevention and/or therapy of ischaemia and reperfusion damage.

The elucidation of the molecular mechanism of cell death is the subject of intense biomedical research efforts. The aim is to find specifically active compounds which have modulating action in this process. When the individual biochemical steps resulting in cell death were examined, attention was drawn to poly(ADP-ribose)-synthetase (PARS), a protein which is expressed strongly in the cell nucleus and which is involved in deoxyribonucleic acid (DNA) damage repair [Szabo and Dawson, Trends in Pharmacological Sciences, 19, 287–298 (1998)].

Activation of PARS plays an important role in N-methyl-D-aspartate (NMDA)- and NO-induced neurotoxicity [Zhang et al., Science, 263, 687–689 (1994); Wallis et al., NeuroReport, 5, 245–248 (1993)], cerebral ischaemia [Endres et al., J. Cereb. Blood Flow Metabol., 17, 1143–1151 (1997)], traumatic brain injuries [Wallis et al., Brain Res., 710, 169–177 (1996)] and ischaemia/reperfusion damage to heart and skeletal muscle [Thiemermann et al., Proc. Nat. Acad. Sci., 94, 679–683 (1997)]. In addition, inhibition of PARS appears to have a positive effect on the therapy of arthritis [Szaboet al., Japanese J. Pharm., 75, Supp. I:102 (1997)], diabetes [Shimabukuro et al., J. Clin. Invest., 100, 290–295 (1997)] and endotoxic or septic shock [Zingarelli et al., Shock, 5, 258–264 (1996)], radiosensitization of hypoxic tumour cells [Weltin et al., Oncol. Res., 6, 399–403 (1994)], chronic colitis [Jijon et al., Am. J. Physiol. Gastrointest. Liver Physiol., 279, G641–51 (2000)], sudden deafness [Tabuchi et al., Ann. Otol. Rhinol. Laryngol., 110(2), 118–21 (2001)], inflammatory pulmonary disorders, such as, for example, asthma and chronic bronchitis [Cuzzocrea et al., Eur. J. Pharm., 342, 67–76 (1998)] and cancer.

PARS, an enzyme which constructs polymeric ADP-ribose units from nicotinamide adenosine dinucleotide ($NAD^+$) as substrate, is activated when the DNA is damaged by single- or double-strand breaks. The polymeric ADP-ribose units formed are attached both to PARS itself and to other proteins, for example histones, topoisomerases and polymerases.

Increased activation of PARS results in a massive $NAD^+$ consumption. The marked decrease of the $NAD^+$ concentration and the resulting impediment of ATP synthesis (decrease of the ATP concentration) causes deterioration of the energetic state of the cell, which may lead to premature cell death (necrosis).

In the heart, reperfusion of ischaemic myocardium results in the generation of radicals, neutrophil infiltration, destruction of the myocardial tissue structure, contraction dysfunctions and necrosis. The $H_2O_2$ generated during the reperfusion phase reacts rapidly with NO, forming peroxynitrite. NO, peroxynitrite and $H_2O_2$ cause DNA strand breaks, thus resulting in overstimulation of PARS.

A further important point in the case of reperfusion damage is the accumulation of neutrophils in the reperfused myocardium. Activation of PARS increases the infiltration of neutrophils by stimulating the expression of P-selectin and ICAM-1.

Healthy PARS knock-out mice capable of reproduction are substantially protected against reperfusion damage. Infiltration of neutrophils is reduced by 50% and the structure of the myocardial tissue remains intact during the reperfusion phase.

In cases of ischaemia and reperfusion damage to heart and brain, low-molecular-weight PARS inhibitors, such as, for example, 3-aminobenzamide and 1,5-dihydroxyisoquinoline, protect the tissue against necrotic cell death (reduction of the infarct size by 30 to 48%) and delay myocardial and neuronal dysfunction.

However, the PARS inhibitors hitherto tested in animal experiments have various disadvantages. Thus, for example, 3-aminobenzamide is an unspecific PARS inhibitor which also inhibits cytochrome $P_{450}$ (Eriksson et al., Toxicology and applied Pharmacology, 136, 324–331 (1996)); in contrast, 5-iodo-6-amino-1,2-benzopyrone has serious side-effects (Szabo and Dawson, Trends in Pharmacol. Sciences, 19, 287–298 (1998)). Moreover, most inhibitors are not very potent and are therefore only efficacious in animals at a relatively high dosage (Thiemermann et al., Proc. Natl. Acad. Sci., 94, 679–683 (1997)).

JP-A-032645679 and Chem. Pharm. Bull. 38 (10), 2726–2732 (1990) disclose bicyclic 2,4-(1H,3H)-pyrimidinediones as $5-HT_2$ antagonists for the treatment of cardiovascular diseases, depression and other mental disorders. U.S. Pat. No. 5,859,014 discloses tetrahydroquinazolinedione derivatives as $\alpha_1$ adrenergic receptor antagonists for the treatment of prostate hypertrophy. WO-A-00/42025 describes dihydropyrimidinones as PARS inhibitors. DE-A-1959705 and DE-A-2126148 list uracil derivatives for preparing crop protection agents. DE-A-2142317 mentions uracil derivatives having hypnotic properties. Furthermore, various bridged uracils are described in the literature as nucleoside analogues with potential antiviral action (for example Nucleosides Nucleotides 13 (1–3), 177–196; 13 (4), 891–902 (1994) and J. Med. Chem. 39 (3), 789–795 (1996)).

Accordingly, it is an object of the present invention to provide novel substances for the prevention and/or therapy of disorders, in particular of ischaemia and reperfusion damage.

Here, the compounds according to the invention presumably act as inhibitors of poly(ADP-ribose)-synthetase (PARS).

The present invention relates to compounds of the formula (I)

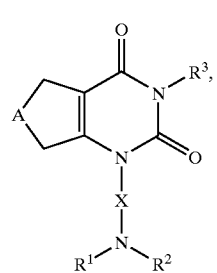

(I)

in which

A represents a ring member selected from the group consisting of:
—D—,
—$CH_2$—D—,
—D—$CH_2$—,
—CH═CH—$CH_2$—,
—$CH_2$—CH═CH—,
—$CH_2$—$CH_2$—D—,
—D—$CH_2$—$CH_2$ and
—$CH_2$—D—$CH_2$—, in which
D represents —$CH_2$—, —O— or —S—, X represents $(C_2–C_{10})$-alkylene or $(C_3–C_8)$-cycloalkylene which are optionally mono- or polysubstituted, independently of one another, by substituents selected from the group consisting of $(C_1–C_6)$-alkoxy, hydroxyl, amino, mono- and di-$(C_1–C_6)$-alkylamino and oxo, $R^1$ represents hydrogen, $(C_1–C_6)$-alkyl which is optionally mono- or polysubstituted by halogen, or represents $(C_3–C_8)$-cycloalkyl, $R^2$ represents a group of the formula —$SO_2$—$R^4$, —$SO_2$—$NR^5R^6$, —CO—$R^7$, —CO—$NR^8R^9$ or —CO—$OR^{10}$, in which $R^4$ represents $(C_1–C_6)$-alkyl or $(C_3–C_8)$-cycloalkyl which are optionally substituted by $(C_1–C_4)$-alkoxy, $(C_6–C_{10})$-aryl, 5- to 10-membered heteroaryl having up to 4 heteroatoms from the group consisting of N, O and/or S, or up to trisubstituted by halogen, where the aryl or heteroaryl radicals for their part are optionally substituted by hydroxyl, $(C_1–C_4)$-alkoxy, $(C_1–C_4)$-alkyl, halogen, cyano or nitro, or represents a group of the formula

—G—E in which
E represents $(C_6–C_{10})$-aryl or a 5- to 13-membered saturated, partially unsaturated or aromatic heterocycle having up to four heteroatoms from the group consisting of N, O and S, where the ring systems are in each case optionally substituted up to five times by identical or different substituents selected from the group consisting of nitro, cyano, halogen, optionally benzamido-substituted $(C_1–C_6)$-alkyl, trifluoromethyl, $(C_3–C_6)$-cycloalkyl, hydroxyl, oxo, $(C_1–C_6)$-alkoxy, carboxyl, $(C_1–C_6)$-alkoxycarbonyl, $(C_1–C_6)$-alkanoyl, amino, aminocarbonyl, mono- and di-$(C_1–C_6)$-alkylaminocarbonyl, $(C_1–C_6)$-alkanoylamido, $(C_1–C_6)$-alkylsulphonyl, $(C_1–C_6)$-alkylthio, optionally $(C_1–C_4)$-alkyl-, halogen- or nitro-substituted phenylsulphonyl,

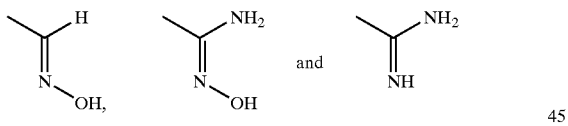

and

G is absent or represents $(C_6–C_{10})$-arylene or 5- to 10-membered heteroarylene having up to 4 heteroatoms from the group consisting of N, O and S, which are in each case optionally substituted up to three times by identical or different substituents selected from the group consisting of nitro, cyano, halogen, $(C_1–C_6)$-alkyl, trifluoromethyl, $(C_3–C_6)$-cycloalkyl, hydroxyl, $(C_1–C_6)$-alkoxy, carboxyl, $(C_1–C_6)$-alkoxycarbonyl, $(C_1–C_6)$-alkanoyl, amino, aminocarbonyl, mono- and di-$(C_1–C_6)$-alkylaminocarbonyl, $(C_1–C_6)$-alkanoylamido, $(C_1–C_6)$-alkylsulphonyl and $(C_1–C_6)$-alkylthio, $R^5$ and $R^6$ independently of one another each represent hydrogen, $(C_3–C_8)$-cycloalkyl, $(C_1–C_6)$-alkyl, $(C_6–C_{10})$-aryl or 5- to 10-membered heteroaryl which, independently of one another, are in each case optionally substituted by $(C_1–C_4)$-alkoxy, hydroxyl, cyano, carboxyl, $(C_1–C_4)$-alkoxycarbonyl, up to three times by halogen, by $(C_6–C_{10})$-aryl or by 5- to 10-membered heteroaryl, where the aryl and hetaryl radicals for their part are optionally substituted by hydroxyl, $(C_1–C_4)$-alkoxy, $(C_1–C_4)$-alkyl, halogen, cyano or nitro, or $R^5$ and $R^6$ together with the nitrogen atom to which they are attached form a saturated 3- to 7-membered heterocycle in which optionally one carbon ring member is replaced by a further heteroatom from the group consisting of nitrogen, oxygen and sulphur and which is optionally substituted by $(C_1–C_4)$-alkyl, hydroxyl, $(C_1–C_4)$-alkoxy, oxo, carboxyl or $(C_1–C_4)$-alkoxycarbonyl, $R^7$ represents $(C_1–C_6)$-alkyl or $(C_3–C_8)$-cycloalkyl which are optionally substituted by $(C_1–C_4)$-alkoxy, $(C_6–C_{10})$-aryl, 5- to 10-membered heteroaryl having up to 4 heteroatoms from the group consisting of N, O and S or up to three times by halogen, where the aryl or heteroaryl radicals for their part are optionally substituted by hydroxyl, $(C_1–C_4)$-alkoxy, $(C_1–C_4)$-alkyl, halogen, cyano or nitro, or represents a group of the formula

—G—E in which
E represents $(C_6–C_{10})$-aryl or a 5- to 13-membered saturated, partially unsaturated or aromatic heterocycle having up to four heteroatoms from the group consisting of N, O and S, where the ring systems are in each case optionally substituted up to five times by identical or different substituents selected from the group consisting of nitro, cyano, halogen, optionally benzamido-substituted $(C_1–C_6)$-alkyl, trifluoromethyl, $(C_3–C_6)$-cycloalkyl, hydroxyl, oxo, $(C_1–C_6)$-alkoxy, carboxyl, $(C_1–C_6)$-alkoxycarbonyl, $(C_1–C_6)$-alkanoyl, amino, aminocarbonyl, mono- and di-$(C_1–C_6)$-alkylaminocarbonyl, $(C_1–C_6)$-alkanoylamido, $(C_1–C_6)$-alkylsulphonyl, $(C_1–C_6)$-alkylthio and optionally $(C_1–C_4)$-alkyl-, halogen- or nitro-substituted phenylsulphonyl, and G is absent or represents $(C_6–C_{10})$-arylene or 5- to 10-membered heteroarylene having up to 4 heteroatoms from the group consisting of N, O and S, which are in each case optionally substituted up to three times by identical or different substituents selected from the group consisting of nitro, cyano, halogen, $(C_1–C_6)$-alkyl, trifluoromethyl, $(C_3–C_6)$-cycloalkyl, hydroxyl, $(C_1–C_6)$-alkoxy, carboxyl, $(C_1–C_6)$-alkoxycarbonyl, $(C_1–C_6)$-alkanoyl, amino, aminocarbonyl, mono- and di-$(C_1–C_6)$-alkylaminocarbonyl, $(C_1–C_6)$-alkanoylamido, $(C_1–C_6)$-alkylsulphonyl and $(C_1–C_6)$-alkylthio, $R^8$ and $R^9$ independently of one another each represent hydrogen, $(C_3–C_8)$-cycloalkyl or $(C_1–C_6)$-alkyl which can in each case optionally be substituted by $(C_1–C_4)$-alkoxy, hydroxyl, cyano, carboxyl, $(C_1–C_4)$-alkoxycarbonyl, up to three times by halogen, by $(C_6–C_{10})$-aryl or by 5- to 10-membered heteroaryl, where the aryl and hetaryl radicals for their part are optionally substituted by hydroxyl, $(C_1–C_4)$-alkoxy, $(C_1–C_4)$-alkyl, halogen, cyano or nitro, or $R^8$ and $R^9$ together with the nitrogen atom to which they are attached form a saturated 3- to 7-membered heterocycle in which optionally one carbon ring member is replaced by a further heteroatom from the group consisting of nitrogen, oxygen and sulphur and which is optionally substituted by $(C_1-C_4)$-alkyl, hydroxyl, $(C_1-C_4)$-alkoxy, oxo, carboxyl or $(C_1-C_4)$-alkoxycarbonyl, $R^{10}$ represents $(C_1-C_6)$-alkyl, $(C_3-C_8)$-cycloalkyl or $(C_6-C_{10})$-aryl which are optionally mono- or polysubstituted by hydroxyl, $(C_1-C_4)$-alkoxy, halogen, cyano or nitro, or $R^1$ and $R^2$ together with the nitrogen atom to which they are attached form a saturated 5- to 10-membered mono- or bicyclic heterocycle, which has a carbonyl or sulphonyl group directly adjacent to the nitrogen atom to which $R^1$ and $R^2$ are attached, in which optionally up to two carbon ring members are replaced by oxygen and/or sulphur and which is optionally substituted up to three times by identical or different substituents selected from the group consisting of $(C_1-C_6)$-alkyl, hydroxyl, oxo, $(C_1-C_6)$-alkoxy, carboxyl, $(C_1-C_4)$-alkoxycarbonyl and halogen, and $R^3$ represents hydrogen or $(C_1-C_6)$-alkoxycarbonyl and their pharmaceutically acceptable salts, hydrates and prodrugs.

Depending on the substitution pattern, the compounds of the formula (I) according to the invention can exist in stereoisomeric forms which are either like image and mirror image (enantiomers) or are not like image and mirror image (diastereomers). The invention relates both to the enantiomers or diastereomers and to their respective mixtures. The racemic forms, like the diastereomers, can be separated in a known manner into the stereoisomerically uniform components.

Furthermore, certain compounds of the formula (I) can be present in tautomeric forms. This is known to the person skilled in the art, and such compounds are likewise included in the scope of the invention.

Pharmaceutically aceeptable, i.e. physiologically safe, salts can be salts of the compounds according to the invention with inorganic or organic acids. Preference is given to salts with inorganic acids such as, for example, hydrochloric acid, hydrobromic acid, phosphoric acid or sulphuric acid, or to salts with organic carboxylic or sulphonic acids such as, for example, acetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

Pharmaceutically acceptable salts which may be mentioned include salts with customary bases, such as, for example, alkali metal salts (for example sodium salts or potassium salts), alkaline earth metal salts (for example calcium salts or magnesium salts) or ammonium salts derived from ammonia or organic amines, such as, for example, diethylamine, triethylamine, ethyldiisopropylamine, procaine, dibenzylamine, N-methylmorpholine, dihydroabietylamine or methylpiperidine.

According to the invention, "hydrates" are forms of the compounds of the formula (I) above which, in the solid or liquid state, form a molecular compound (solvate) by hydration with water. Examples of hydrates are sesquihydrates, monohydrates, dihydrates and trihydrates. Equally suitable are the hydrates of salts of the compounds according to the invention.

According to the invention, "prodrugs" are derivatives of the compounds of the formula (I) above which for their part can be biologically active or inactive, but which, following administration, can be converted under physiological conditions (for example metabolically, solvolytically or otherwise) into the corresponding biologically active form.

Halogen represents fluorine, chlorine, bromine and iodine. Preference is given to chlorine and fluorine.

$(C_1-C_{10})$-Alkyl represents a straight-chain or branched alkyl radical having 1 to 10 carbon atoms. Examples which may be mentioned are: methyl, ethyl, n-propyl, isopropyl, n-butyl, isobutyl, tert-butyl, n-pentyl, n-hexyl, n-octyl and n-decyl. The corresponding alkyl groups having fewer carbon atoms, such as, for example, $(C_2-C_{10})$-alkyl, $(C_1-C_6)$-alkyl and $(C_1-C_4)$-alkyl, are derived analogously from this definition. In general, $(C_1-C_4)$-alkyl is preferred.

Also derived from this definition is the meaning of the corresponding component of other more complex substituents, such as, for example, in the case of monoalkylamino, di-acylamino, alkylsulphonyl, alkylthio or alkylene, in which an alkyl radical defined as above is attached via two positions Mono- or di-$(C_1-C_4)$-alkylaminocarbonyl represents an amino group which is attached via a carbonyl group and has one or two identical or different straight-chain or branched alkyl substituents having in each case 1 to 4 carbon atoms. Examples which may be mentioned are: methylaminocarbonyl, ethylaminocarbonyl, n-propylaminocarbonyl, isopropyl-aminocarbonyl, t-butylaminocarbonyl, N,N-dimethylaminocarbonyl, N,N-diethyl-aminocarbonyl, N-ethyl-N-methylamino-carbonyl, N-methyl-N-n-propylaminocarbonyl, N-isopropyl-N-n-propylamino-carbonyl and N-t-butyl-N-methylamino-carbonyl.

$(C_1-C_6)$-Alkylthio represents a straight-chain or branched alkylthio radical having 1 to 6 carbon atoms. Preference is given to a straight-chain or branched alkylthio radical having 1 to 4 carbon atoms. Examples which may be mentioned are: methylthio, ethylthio, n-propylthio, isopropylthio, t-butylthio, n-pentylthio and n-hexylthio.

$(C_3-C_8)$-Cycloalkyl represents a cyclic alkyl radical having 3 to 8 carbon atoms. Examples which may be mentioned are: cyclopropyl, cyclobutyl, cyclopentyl, cyclohexyl, cycloheptyl or cyclooctyl. The corresponding cycloalkyl groups having fewer carbon atoms, such as, for example, $(C_3-C_6)$-cycloalkyl, are derived analogously from this definition. Preference is given to cyclopropyl, cyclopentyl and cyclohexyl.

The meaning of the corresponding component of other more complex substitutents, such as, for example, in the case of cycloalkylene, in which a cycloalkyl radical as defined above is attached via two positions, is also derived from this definition.

$(C_1-C_6)$-Alkoxy represents a straight-chain or branched alkoxy radical having 1 to 6 carbon atoms. Examples which may be mentioned are: methoxy, ethoxy, n-propoxy, isopropoxy, n-butoxy, isobutoxy, tert-butoxy, n-pentoxy and n-hexoxy. The corresponding alkoxy groups having fewer carbon atoms, such as, for example, $(C_1-C_4)$-alkoxy, are derived analogously from this definition. In general, $(C_1-C_4)$-alkoxy is preferred.

The meaning of the corresponding component of other more complex substitutents, such as, for example, alkoxycarbonyl, in which an alkoxy radical as defined above is attached via a carbonyl group is also derived from this definition.

$(C_1-C_6)$-Alkanoyl represents a straight-chain or branched alkyl radical having 1 to 6 carbon atoms which carries a doubly attached oxygen atom in the 1-position and is attached via the 1-position. Examples which may be mentioned are: formyl, acetyl, propionyl, n-butyryl, i-butyryl, pivaloyl and n-hexanoyl. The corresponding alkanoyl groups having fewer carbon atoms, such as, for example, ($C_1$–$C_4$)-alkanoyl, are derived analogously from this definition. In general, preference is given to ($C_1$–$C_4$)-alkanoyl.

($C_1$–$C_6$)-Alkanoylamido represents an alkanoyl radical as defined above which is attached via an —NH— group.

($C_6$–$C_{10}$)-Aryl represents an aromatic radical having 6 to 10 carbon atoms. Examples which may be mentioned are: phenyl and naphthyl.

The meaning of the corresponding component of other more complex substituents, such as, for example, arylene, in which an aryl radical as defined above is attached via two positions, is also derived from this definition.

5- to 13-membered heteroaryl or a 5- to 13-membered aromatic heterocycle having up to 4 heteroatoms from the group consisting of N, O and S represents a mono-, bi- or tricyclic heteroaromatic which is attached via a ring carbon atom of the heteroaromatic or, if appropriate, via a ring nitrogen atom of the heteroaromatic. Examples which may be mentioned are: pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolicenyl, indolyl, benzo[b]thienyl, benzo[b]furyl, benzothiadiazolyl, indazolyl, quinolyl, isoquinolyl, naphthyridinyl, quinazolinyl. The corresponding heterocycles having a smaller ring size, such as, for example, 5- or 6-membered aromatic heterocycles, or else heterocycles having fewer heteroatoms, such as, for example, those having up to 3 heteroatoms from the group consisting of N, O and S, are derived analogously from this definition. In general, 5- or 6-membered aromatic heterocycles having up to 3 heteroatoms from the group consisting of N, O and S, such as, for example, pyridyl, pyridyl-N-oxide, pyrimidyl, pyridazinyl, furyl, imidazolyl and thienyl are preferred.

The meaning of the corresponding component of other more complex substituents, such as, for example, heteroarylene, in which a heteroaryl radical as defined above is attached via two positions, is also derived from this definition.

A 5- to 13-membered saturated or partially unsaturated heterocycle having up to 4 heteroatoms from the group consisting of N, O and S represents a mono-, bi- or tricyclic heterocycle which may contain one or more double bonds and which is attached via a ring carbon atom or a ring nitrogen atom. Examples which may be mentioned are: tetrahydrofuryl, pyrrolidinyl, pyrrolinyl, piperidinyl, 1,2-dihydropyridinyl, 1,4-dihydropyridinyl, piperazinyl, morpholinyl, morpholinyl-N-oxide, thiomorpholinyl, azepinyl, 1,4-diazepinyl and cyclohexyl. Preference is given to piperidinyl, morpholinyl and pyrrolidinyl.

The corresponding heterocycles having a different ring size, such as, for example, 3- to 7-membered heterocycles, are derived analogously from this definition.

Preference is given to compounds of the formula (I) according to the invention in which A represents a ring member —$CH_2$—D— or —D—$CH_2$—, in which
  D represents —$CH_2$—, —O— or —S—,
X represents ($C_2$–$C_4$)-alkylene or cyclohexylene,
$R^1$ represents hydrogen, ($C_1$–$C_4$)-alkyl which is optionally substituted up to three times by fluorine, or ($C_3$–$C_6$)-cycloalkyl,
$R^2$ represents a group of the formula —$SO_2$—$R^4$, —CO—$R^7$ or —CO—$OR^{10}$, in which
  $R^4$ represents ($C_1$–$C_4$)-alkyl which is optionally substituted up to three times by fluorine, or represents a group of the formula

—G—E in which
  E represents ($C_6$–$C_{10}$)-aryl or a 5- to 13-membered saturated, partially unsaturated or aromatic heterocycle having up to three heteroatoms from the group consisting of N, O and S, where the ring systems are in each case optionally substituted up to three times by identical or different substituents selected from the group consisting of nitro, cyano, fluorine, chlorine, bromine, optionally benzamido-substituted ($C_1$–$C_4$)-alkyl, trifluoromethyl, ($C_3$–$C_6$)-cycloalkyl, hydroxyl, oxo, ($C_1$–$C_4$)-alkoxy, carboxyl, ($C_1$–$C_4$)-alkoxycarbonyl, ($C_1$–$C_4$)-alkanoyl, amino, aminocarbonyl, mono- and di-($C_1$–$C_4$)-alkylaminocarbonyl, ($C_1$–$C_4$)-alkanoylamido, ($C_1$–$C_4$)-alkylsulphonyl, ($C_1$–$C_4$)-alkylthio and optionally methyl-, fluorine-, chlorine-, bromine- or nitro-substituted phenylsulphonyl, and
  G is absent or represents ($C_6$–$C_{10}$)-arylene or 5- or 6-membered heteroarylene having up to three heteroatoms from the group consisting of N, O and S, which are in each case optionally substituted up to three times by identical or different substituents selected from the group consisting of nitro, cyano, fluorine, chlorine, bromine, ($C_1$–$C_4$)-alkyl, trifluoromethyl, ($C_3$–$C_6$)-cycloalkyl, hydroxyl, ($C_1$–$C_4$)-alkoxy, carboxyl, ($C_1$–$C_4$)-alkoxycarbonyl, ($C_1$–$C_4$)-alkanoyl, amino, aminocarbonyl, mono- and di-($C_1$–$C_4$)-alkylaminocarbonyl, ($C_1$–$C_4$)-alkanoylamido, ($C_1$–$C_4$)-alkylsulphonyl and ($C_1$–$C_4$)-alkylthio,
  $R^7$ represents ($C_6$–$C_{10}$)-aryl which is optionally substituted by nitro,
  $R^{10}$ represents ($C_1$–$C_4$)-alkyl which is optionally substituted up to three times by chlorine, or
$R^1$ and $R^2$ together with the nitrogen atom to which they are attached form a saturated 5- to 10-membered mono- or bicyclic heterocycle
  which has a carbonyl group directly adjacent to the nitrogen atom to which $R^1$ and $R^2$ are attached,
  in which optionally up to two carbon ring members are replaced by oxygen and/or sulphur and
  which is optionally substituted up to three times by identical or different substituents selected from the group consisting of ($C_1$–$C_4$)-alkyl, hydroxyl, oxo, ($C_1$–$C_4$)-alkoxy, carboxyl, ($C_1$–$C_4$)-alkoxycarbonyl and halogen, and
$R^3$ represents hydrogen and their pharmaceutically acceptable salts, hydrates and prodrugs.

Particular preference is given to compounds of the formula (I) according to the invention in which A represents a ring member —$CH_2$—D— or —D—$CH_2$—, in which
  D represents —$CH_2$—, —O— or —S—,
X represents ($C_2$–$C_4$)-alkylene,
$R^1$ represents hydrogen, ($C_1$–$C_4$)-alkyl which is optionally substituted up to three times by fluorine, or ($C_3$–$C_6$)-cycloalkyl, $R^2$ represents a group of the formula

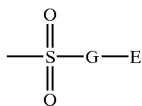

in which
E represents $(C_6–C_{10})$-aryl or a 5- to 13-membered saturated, partially unsaturated or aromatic heterocycle having up to three heteroatoms from the group consisting of N, O and S, where the ring systems are in each case optionally substituted up to three times by identical or different substituents selected from the group consisting of nitro, cyano, fluorine, chlorine, bromine, optionally benzamido-substituted $(C_1–C_4)$-alkyl, trifluoromethyl, $(C_3–C_6)$-cycloalkyl, hydroxyl, oxo, $(C_1–C_4)$-alkoxy, carboxyl, $(C_1–C_4)$-alkoxycarbonyl, $(C_1–C_4)$-alkanoyl, amino, aminocarbonyl, mono- and di-$(C_1–C_4)$-alkylaminocarbonyl, $(C_1–C_4)$-alkanoylamido, $(C_1–C_4)$-alkylsulphonyl, $(C_1–C_4)$-alkylthio and optionally methyl-, fluorine-, chlorine-, bromine- or nitro-substituted phenylsulphonyl, and G is absent or represents $(C_6–C_{10})$-arylene or 5- or 6-membered heteroarylene having up to three heteroatoms from the group consisting of N, O and S, which are in each case optionally substituted up to three times by identical or different substituents selected from the group consisting of nitro, cyano, fluorine, chlorine, bromine, $(C_1–C_4)$-alkyl, trifluoromethyl, $(C_3–C_6)$-cycloalkyl, hydroxyl, $(C_1–C_4)$-alkoxy, carboxyl, $(C_1–C_4)$-alkoxycarbonyl, $(C_1–C_4)$-alkanoyl, amino, aminocarbonyl, mono- and di-$(C_1–C_4)$-alkylaminocarbonyl, $(C_1–C_4)$-alkanoylamido, $(C_1–C_4)$-alkylsulphonyl and $(C_1–C_4)$-alkylthio, or $R^1$ and $R^2$ together with the nitrogen atom to which they are attached form a saturated 5- to 10-membered mono- or bicyclic heterocycle
which has a carbonyl group directly adjacent to the nitrogen atom to which $R^1$ and $R^2$ are attached,
in which optionally up to two carbon ring members are replaced by oxygen and/or sulphur and
which is optionally substituted up to three times by identical or different substituents selected from the group consisting of $(C_1–C_4)$-alkyl, hydroxyl, oxo, $(C_1–C_4)$-alkoxy, carboxyl, $(C_1–C_4)$-alkoxycarbonyl and halogen, and $R^3$ represents hydrogen
and their pharmaceutically acceptable salts, hydrates and prodrugs.

Very particular preference is given to compounds of the formula (I) according to the invention in which A represents a ring member —$CH_2$—D— or —D—$CH_2$—, in which
D represents —$CH_2$— or —S—,
X represents $(C_2–C_4)$-alkylene,
$R^1$ represents hydrogen, methyl, trifluoromethyl or cyclopropyl.

$R^2$ represents a group of the formula

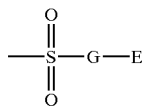

in which
E represents $(C_6–C_{10})$-aryl or a 5- to 10-membered partially unsaturated or aromatic heterocycle having up to three heteroatoms from the group consisting of N, O and S, where the ring systems are in each case optionally substituted up to two times by identical or different substituents selected from the group consisting of nitro, cyano, amino, fluorine, chlorine, bromine, $(C_1–C_4)$-alkyl, trifluoromethyl, $(C_3–C_6)$-cycloalkyl, hydroxyl, oxo and $(C_1–C_4)$-alkoxy, and G is absent or represents phenylene or thienylene, and $R^3$ represents hydrogen,
and their pharmaceutically acceptable salts, hydrates and prodrugs.

Most preference is given to the compounds of Examples, 6, 57, 59, 69, 71, 72 and their pharmaceutically acceptable salts, hydrates and prodrugs.

The present invention also provides a process for preparing the compounds of the formula (I) according to the invention, where Compounds of the formula (II)

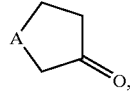

(II)

in which
A is as defined above are reacted with compounds of the formula (III)

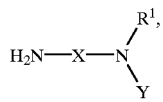

(III)

in which
Y represents $R^2$ or a customary amino protective group and X, $R^1$ and $R^2$ are each as defined above to give compounds of the formula (IV)

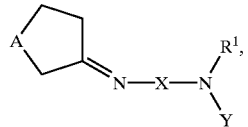

(IV)

in which
Y represents $R^2$ or a customary amino protective group and A, X, $R^1$ and $R^2$ are each as defined above
are subsequently reacted with chlorocarbonyl isocyanate to give compounds of the formula (V)

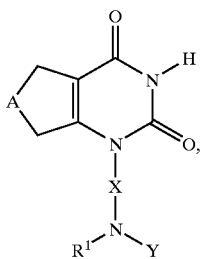

(V)

in which
Y represents R² or a customary amino protective group and A, X, R¹ and R² are each defined above,
Y represents a customary amino protective group, compounds of the formula (V) are, if appropriate, converted, by removal of this protective group, into compounds of the formula (VI)

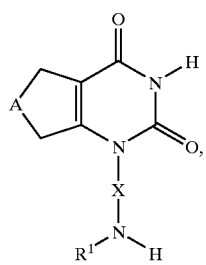

(VI)

in which
A, X and R¹ are each as defined above
and are reacted, if appropriate in the presence of a base, with compounds of the formula (VII)

R²—T          (VII)

in which
R² is as defined above and T represents a leaving group to give compounds of the formula (V) in which
Y represents R² and A, X, R² and R² are each as defined above
and, if appropriate, compounds of the formula (V) are reacted, if appropriate in the presence of a base, with compounds of the formula (VIII)

R³—T          (VIII)

in which
R³ is as defined above, but not hydrogen, and T represents a leaving group to give compounds of the formula (I) in which R³ is as defined above, but not hydrogen,
where, if the compound prepared in this manner contains a bromoaryl or bromohetaryl group in the radical R³, a transition-metal-catalysed coupling reaction with an organotin or organoboron compound by customary methods may follow and/or
where, if the compound prepared in this manner contains an aldehyde group in the radical R³, this aldehyde group may then be converted into the corresponding oxime using customary methods and/or
where, if the compound prepared in this manner contains a cyano group in the radical R³, this cyano group may then be converted via the stage of the corresponding hydroxylamidine, into the corresponding amidine, using customary methods.

The process according to the invention for preparing compounds of the formula (I) can be illustrated in an exemplary, but not limiting, manner by the equations below:

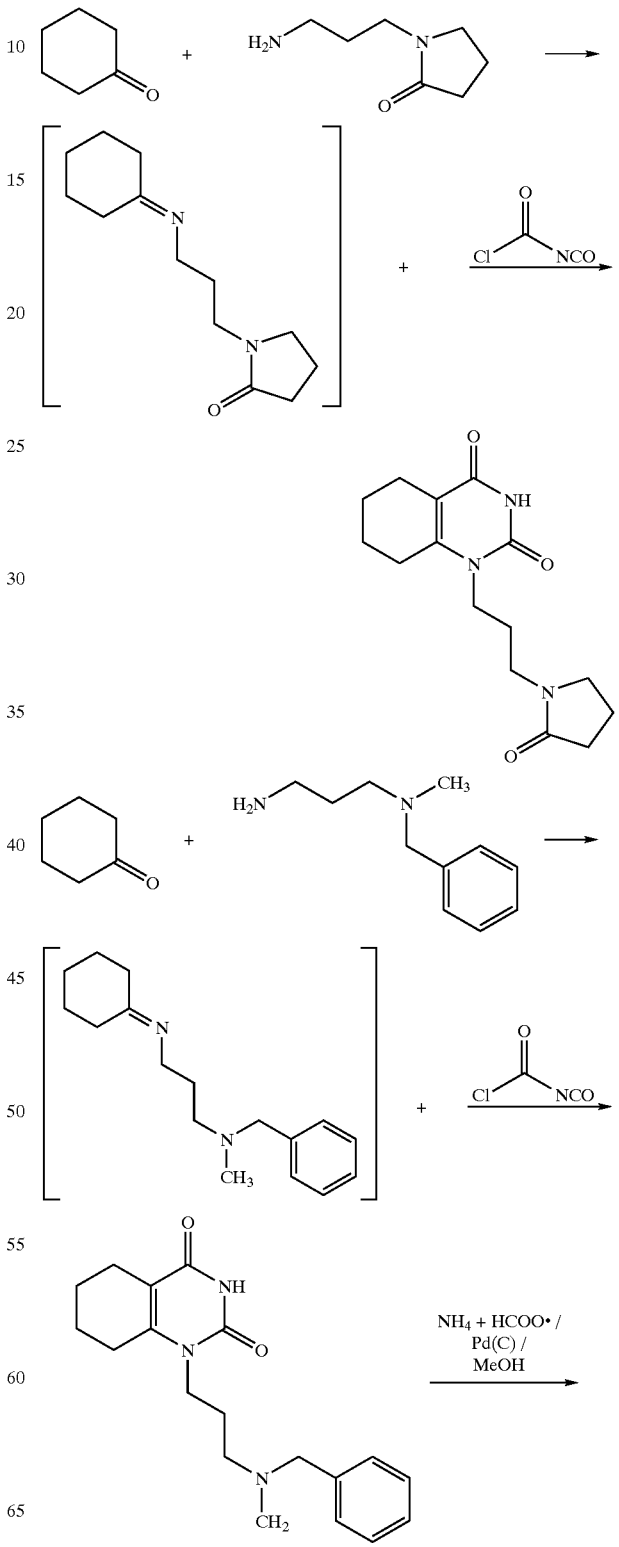

-continued

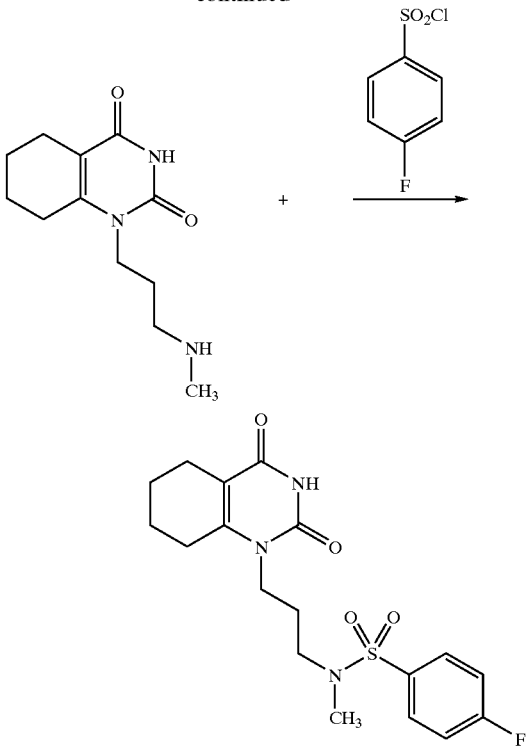

Solvents suitable for the process described above are organic solvents which are inert under the reaction conditions. These include halogenated hydrocarbons, such as dichloromethane, trichloromethane, carbon tetrachloride, 1,2-dichloroethane, trichloroethane, tetrachloroethane, 1,2-dichloroethylene or trichloroethylene, ethers, such as diethyl ether, dioxane, tetrahydrofuran, glycol dimethyl ether or diethylene glycol dimethyl ether, hydrocarbons, such as benzene, xylene, toluene, hexane or cyclohexane, dimethylformamide, dimethyl sulphoxide, acetonitrile, pyridine or hexamethylphosphoric triamide. It is also possible to use solvent mixtures of the solvents mentioned above.

The reactions are generally carried out in a temperature range of from −78° C. to reflux temperature, preferably in the range from 0° C. to reflux temperature.

The reactions can be carried out at atmospheric, elevated or reduced pressure (for example in the range from 0.5 to 5 bar). In general, they are carried out at atmospheric pressure.

Suitable bases are the customary inorganic or organic bases. These preferably include alkali metal hydroxides, such as, for example, sodium hydroxide or potassium hydroxide, or alkali metal carbonates, such as sodium carbonate or potassium carbonate, or sodium methoxide or potassium methoxide or sodium ethoxide or potassium ethoxide or potassium tert-butoxide, or amides, such as sodium amide, lithium bis-(trimethylsilyl)amide or lithium diisopropylamide, or amines, such as triethylamine, diisopropylethylamine, diisopropylamine, 4,N,N-dimethylaminopyridine or pyridine.

Preferred solvent for the reaction of compounds of the formula (II) with compounds of the formula (III) to give compounds of the formula (IV) and the further conversion with chlorocarbonyl isocyanate and to compounds of the formula (V) is toluene. In the reaction of compounds of the formula (VI) with compounds of the formula (VII), pyridine is preferred if $R^2$ is a sulphonyl radical and tetrahydrofuran, dichloromethane or acetonitrile is preferred if $R^2$ is an alkoxycarbonyl radical.

The temperature range for the reaction of compounds of the formula (II) with compounds of the formula (III) to give compounds of the formula (IV) is in particular from 80 to 120° C. The addition of chlorocarbonyl isocyanate in the conversion of compounds of the formula (IV) into compounds of the formula (V) is in particular carried out at room temperature; the further reaction is then carried out in particular in a temperature range from 80 to 120° C. The reaction of compounds of the formula (VI) with compounds of the formula (VII) is, if $R^2$ is a sulphonyl radical, carried out in particular at room temperature.

The reaction of compounds of the formula (II) with compounds of the formula (III) to give compounds of the formula (IV) may, if appropriate, be accelerated by adding catalytic amounts of acid, preferably organic sulphonic acid, in particular camphorsulphonic acid.

Suitable leaving groups T in compounds of the formulae (VII) and (VIII) are, for example: halogen, mesylate, tosylate, triflate or 1-imidazolyl, preferably chlorine.

Suitable amino protective groups for compounds of the formulae (III), (IV) and (V) are the radicals which are customarily used, as described, for example, in T. W. Greene, P. G. M. Wuts, Protective Groups in Organic Synthesis, second edition, New York, 1991. Examples which may be mentioned are: benzyl and BOC (tert-butoxycarbonyl). Removal of the amino protective group in the conversion of compounds of the formula (V) into compounds of the formula (VI) is carried out in the manner customary for the amino protective group in question, as described, for example, in T. W. Greene, P. G. M. Wuts, Protective Groups in Organic Synthesis, second edition, New York, 1991.

The transition-metal-catalysed coupling reaction, which is carried out, if appropriate, of aryl or hetaryl bromides with organotin compounds (Stille coupling) or organoboron compounds (Suzuki coupling) is carried out under the reaction conditions customary for these couplings, in the presence of a catalyst, preferably in the presence of a transition metal catalyst, in particular in the presence of a palladium catalyst (see, for example J. Tsuju, Palladium Reagents and Catalysts, J. Wiley & Sons, 1995), preferably in the solvent dimethylformamide. Preferred transition metal catalysts are palladium(0) or palladium(II) compounds, in particular bis-(triphenylphosphine)-palladium(II) chloride or tetrakis-(triphenylphosphine)-palladium(0). If organoboron compounds are used (Suzuki coupling, review: N. Miyaura, A. Suzuki, Chem. Rev. 1995, 95, 2457–2483), the reaction is carried out, in particular, at a temperature of from 90° C. to 110° C. in the presence of a base, preferably aqueous sodium carbonate solution. If organotin compounds are used (Stille coupling, review: V. Farina, V. Krishnamurthy, W. J. Scott in: The Stille Reaction, 1998, J. Wiley and Sons, New York), the reaction is carried out, in particular, at a temperature of from 110 to 130° C.

The conversion of aldehyde groups into the corresponding oximes and of cyano groups, via the stage of the corresponding hydroxyamidines, into the corresponding amidines, are carried out, if appropriate, using the preparation methods customary for these reactions. Furthermore, reference is made to Examples 108 to 110 in the experimental part.

The compounds of the formulae (II), (III), (VII) and (VIII) are known to the person skilled in the art or can be prepared by customary methods.

The compounds of the formula (I) according to the invention have an unforeseeable useful spectrum of pharmacological activity, and they are therefore particularly suitable for the prophylaxis and/or treatment of disorders.

They can preferably be used in medicaments for the prevention and/or therapy of ischaemic and reperfusion damage in the heart (after an acute infarction), in the brain (after a stroke) or in skeletal muscle, for cardiovascular disorders, such as, for example, unstable angina pectoris and arteriosclerosis, neuronal and neurodegenerative disorders, such as, for example, epilepsy, chronic pain, Alzheimer's disease and Parkinson's disease, traumatic brain injuries, septic shock, and also arthritis, diabetes, chronic colitis, sudden deafness, inflammable pulmonary disorders, such as, for example, asthma and chronic bronchitis, and cancer.

The present invention also relates to the use of the substances of the formula (I) for preparing medicaments and to pharmaceutical compositions for the prophylaxis and/or treatment of the clinical pictures mentioned above.

The present invention furthermore relates to a method for the prophylaxis and/or treatment of the clinical pictures mentioned above using the substances of the formula (I).

In addition, the compounds according to the invention can also be used for the treatment of acute myocardial infarction, including in combination with one or more of the following medicaments which are used for the standard therapy of acute myocardial infarction: calcium channel blockers (such as, for example, nifedipine, diltiazem, verapamil), nitrovasodilators (such as, for example, isosorbide dinitrate, glycerol trinitrate, isosorbide 5-mono-nitrate, molsidomine), beta blockers, (such as, for example, metoprolol, atenolol, propranolol, solatol), platelet aggregation inhibitors (such as, for example, acetylsalicylic acid, triclopidine, clopidrogrel), thrombolytics (fibrinolytics) (such as, for example, streptokinase, alteplase, reteplase, urokinase, anistreplase), anticoagulants (such as, for example, heparin, warfarin, phenprocoumarin, low-molecular-weight heparins), ACE inhibitors (such as, for example, enalapril), glycoprotein IIb/IIIa receptor antagonists (such as, for example, tirofiban, eptifibatide), antiarrhythmics (such as, for example, lidocaine, amiodarone) and beta-adrenergic agonists (such as, for example, dopamine, dobutamine).

A EVALUATION OF THE PHYSIOLOGICAL ACTIVITY

1) Test Description PARS Inhibition Test (in vitro)

The activity of substances as PARS inhibitors is tested in accordance with the method of Ushiro [Ushiro et al., J. Biol. Chem., 262, 2352–2357 (1987)]. To this end, recombinantly expressed (Bac-To-Bac, Baculo virus expression system; Instruction Manual; Life Technologies) human PARS enzyme is activated in a buffer which contains radioactively labelled [$^{14}$C]-NAD$^+$. The poly(ADP-ribose) units that are synthesized are precipitated using trichloroacetic acid, and the proportion of labelled protein is determined by scintillation measurements. Incubation of PARS with inhibitors leads to a decrease in the proportion of labelled protein and thus to a reduced radioactivity.

Inhibition of the PARS activity can be represented as a percentage of PARS inhibition in incubation with different substances or as the concentration at which 50% of the enzyme is inhibited, i.e. as IC$_{50}$ value.

Material
  Buffer:
  100 mM
    Tris-HCl,
    pH 7.4
  10 mM
    MgCl$_2$
  1 mM
    dithiothreitol (DTT)

Tris-HCl and MgCl$_2$ are dissolved in water, DTT is added from an aqueous 100 mM stock solution (stored at −20° C.) and the pH is adjusted with concentrated HCl to 7.4.

DNA:

1 mg/ml of calf thymus DNA 1 mg/ml of calf thymus DNA (from Sigma) is dissolved in water and sonicated to induce strand breaks. 500 μl aliquots were stored at −20° C.

Histones:

10 mg/ml of type IIA histones, calf thymus 10 mg/ml of lyophilized histones (from Sigma) are dissolved in water.

500 μl aliquots are stored at −20° C.

NAD$^+$ Mix:

2 mM NAD$^+$ in buffer,

NAD$^+$ (from Sigma) solutions are prepared freshly before each test.

In each case 3 μl of labelled [$^{14}$C]-NAD$^+$ (2.8 kBq, from Amersham) are added to 7 μl of cold NAD$^+$ solution.

Trichloroacetic acid (TCA):

TCA is stored at 4° C. as a 10% strength by weight solution.

PARS:

Human PARS protein is expressed recombinantly in the baculo virus system (Bac-To-Bac, Baculo virus expression system; Instruction Manual; Life Technologies) and purified. 500 μl aliquots are stored at −80° C.

Methods

The compounds to be tested are dissolved in DMSO (dimethyl sulphoxide) at a concentration of 10 mM. The assay is carried out in deep 96-well plates. Per well, 70 μl of buffer, 10 μl of DNA, 10 μl of histones, 10 μl of NAD$^+$/[$^{14}$C]-NAD$^+$ mix and 0.5–5 μl of PARS (about 10,000 cpm/test) are combined with 1 μl of the compounds (final concentration 0.001–10 μM), to give a total volume of about 110 μl. The mixture is incubated at room temperature for 10 min, and 1 μl of ice-cold TCA solution is then added, and the precipitated labelled proteins are sucked onto a filter paper (printed filter mat A; from Wallac) using a harvester (from Scatron). The filter is dried, sealed together with a scintillation sheet (Multilex A; from Wallac) and measured in a β counter for 1 min per well.

Results of the PARS Inhibition Test

In addition to the substances described in this application, the known PARS inhibitor 1,5-dihydroxyisoquinoline (DHCH) is tested as reference substance. The results of the test are stated as IC$_{50}$ values for the inhibition of PARS.

The results are shown in Table 1:

TABLE 1

| PARS inhibition (in vitro) | |
|---|---|
| Example | IC$_{50}$ [nM] |
| 2 | 0.02 |
| 4 | 0.08 |
| 6 | 0.009 |
| 17 | 0.025 |
| 28 | 0.08 |
| 59 | 0.04 |

2) Test Description Cell Protection Assay (in vitro)

In accordance with a method described by Bowes [Bowes et al., Br. J. Pharmacol., 124, 1760–1766 (1998)], the ability of PARS inhibitors to protect cells against cell death induced by incubation with $H_2O_2$ is examined in a cell protection assay. Incubation of endothelial cells with $H_2O_2$ results in the generation of DNA strand breaks which in turn activate PARS, resulting in a drastic energy decrease in the cells and in cell death. Living cells are quantified by a fluorimetric redox indicator (Alamar blue), which is converted in the electron transport system of the mitochondria.

Specifically, 7500 MHEC5-T cells/well (DSM ACC 336; German collection of microorganisms and cell cultures) are sown in 4 replications on a 96-well plate. After 24 hours, the cells are incubated with 3 mM aqueous $H_2O_2$ solution and differing concentrations of the substances in the presence of 6% by volume of Alamar blue solution in the medium at 37° C. for 5 hours. The reference substance used is 10 $\mu$M 1,5-dihydroxyisoquinoline (DHCH) solution. After the incubation, the fluorescence is measured at an excitation wavelength of 530–560 nm and an emission wavelength of 590 nm. The percentage for the cell protection is calculated as the difference between the living cells treated only with $H_2O_2$ and the cells treated with $H_2O_2$ and PARS inhibitors. The internal standard used is 10 $\mu$M DHCH, which is defined as 100% protection. The results obtained for the other substances are compared to this value.

Results of the cell protection assays:

Examples of the protection of endothelial cells by PARS inhibitors are listed in Table 2 below. The $EC_{50}$ values indicate the concentration at which 50% of maximum cell protection is reached, maximum protection by 10 $\mu$M DHCH being defined as 100%. DHCH has an $EC_{50}$ value of 2 $\mu$M.

TABLE 2

Cell protection (in vitro)

| Example | $EC_{50}$ [nM] |
|---------|----------------|
| 2 | 0.5 |
| 55 | 0.4 |
| 57 | 0.3 |
| 58 | 0.4 |
| 59 | 0.25 |
| 61 | 0.5 |
| 67 | 0.05 |

3) Test Description "Working Heart" Model (in vivo)

For tests on isolated hearts in the "working heart" mode [Bardenheuer and Schrader, Circulation Res., 51, 263 (1983)], isolated hearts of rats are subjected to a 60-minute "low-flow" phase to generate global ischaemia, and the action of the substances with respect to the reestablishment of the pressure in the left ventricle (LVPmax) and the contractile force (dP/dt) during the reperfusion phase is examined. The control substance used is 1,5-dihydroxyisoquinoline.

The present invention also relates to medicaments and pharmaceutical compositions comprising at least one compound of the formula (I), preferably together with one or more pharmacologically acceptable auxiliaries or excipients, and to their use for the abovementioned purposes.

The active compound can act systemically and/or locally. To this end, it can be administered in a suitable manner, such as, for example, orally, parenterally, pulmonarily, nasally, sublingually, lingually, buccally, rectally, transdermally, conjunctivally, otically or as an implant.

For these administration routes, the active compound can be administered in suitable administration forms.

Administration forms suitable for oral administration are known administration forms which release the active compound rapidly and/or in modified form, such as, for example, tablets (uncoated and also coated tablets, for example enterically coated tablets), capsules, sugar-coated tablets, granules, pellets, powders, emulsions, suspensions and solutions.

Parenteral administration can be effected by circumventing a bioabsorption step (in an intravenous, intraarterial, intracardial, intraspinal or intralumbal manner), or via bioabsorption (intramuscularly, subcutaneously, intracutaneously, percutaneously or intraperitoneally). Administration forms suitable for parenteral administration are, inter alia, preparations for injection and infusion in the form of solutions, suspensions, emulsions, lyophilisates and sterile powders.

Medicinal forms suitable for the other administration routes are, for example, medicinal forms for inhalation (inter alia powder inhalators, nebulizers), nasal drops/solutions, sprays; tablets or capsules to be administered lingually, sublingually or buccally, suppositories, preparations for ears or eyes, vaginal capsules, aqueous suspensions (lotions, agitated mixtures), lipophilic suspensions, ointments, creams, milk, pastes, powder for spreading or implants.

The active compounds can be converted in a manner known per se into the administration forms listed. This is effected using inert non-toxic, pharmaceutically suitable auxiliaries. These include, inter alia, excipients (for example microcrystalline cellulose), solvents (for example liquid polyethylene glycols), emulsifiers (for example sodium dodecyl sulphate), dispersants (for example polyvinylpyrrolidone), synthetic and natural biopolymers (for example albumin), stabilizers (for example antioxidants such as ascorbic acid), colorants (for example inorganic pigments, such as iron oxides), or flavour- and/or odour-masking substances.

In the pharmaceutical preparations listed above, the therapeutically active compounds should be present in a concentration of from about 0.1 to 99.5, preferably from about 0.5 to 95, % by weight of the total mixture, i.e. the active compound should be present in amounts sufficient to achieve the dosage range indicated.

In addition to the compounds of the formula (I) according to the invention, the pharmaceutical preparations listed above may also comprise other pharmaceutically active compounds.

In general, it has been found to be advantageous both in human and veterinary medicine to administer the active compound(s) according to the invention in total amounts of from about 0.1 to about 500, preferably from 1 to 100, mg/kg of body weight per 24 hours, if appropriate in the form of a plurality of individual doses, to obtain the desired results. An individual dose preferably comprises the active compound (s) according to the invention in amounts of from about 0.1 to 80, in particular from 1 to 30, mg/kg of body weight.

In spite of this, it may be necessary, if appropriate, to depart from the amounts mentioned, namely depending on the body weight or on the type of administration route, on the individual response to the medicament, the manner of its formulation and the time or interval at which administration takes place. Thus, in some cases it may be adequate to manage with less than the abovementioned minimum amount, while in other cases the upper limit mentioned has to be exceeded.

The present invention is illustrated below on the basis of the following preferred examples, which, however, in no way limit the invention.

Unless indicated otherwise, all percentages in the examples below are based on weight; in the case of solvent mixtures, the ratios given are by volume.

B PREPARATION EXAMPLES

Example 1

1-[3-(2-Oxo-1-pyrrolidinyl)propyl]-5,6,7,8-tetrahydro-2,4(1H,3H)-quinazolinedione

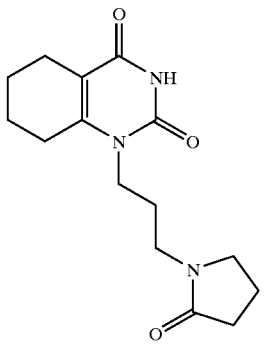

A solution of 1.14 ml (11.0 mmol) of cyclohexanone and 1.42 g (10.0 mmol) of 1-(3-aminopropyl)-2-pyrrolidone [D. J. Bergmann et al., Tetrahedron, 17449 (1997)] in 20 ml of toluene is treated with a spatula tip of camphorsulphonic acid and boiled for 3 hours using a Dean-Stark separator. After this time, the mixture is allowed to cool to room temperature, and 0.97 ml (12.0 mmol) of chlorocarbonyl isocyanate are added. The mixture is once more heated at reflux. After 40 minutes, the reaction has ended. The reaction mixture is partitioned between ethyl acetate and saturated sodium dihydrogen phosphate solution. The organic extract is washed with water and dried over sodium sulphate. Since the aqueous phase also contains product, the aqueous phase is evaporated to dryness and the resulting residue is stirred with methanol. The methanolic extract is combined with the ethyl acetate phase and concentrated and the product is purified by column chromatography (silica gel, ethyl acetate/methanol 4:1). The product fraction is evaporated to dryness and the residue is recrystallized from ethyl acetate. This gives 465 mg (1.6 mmol; 16% yield) of a pale yellow solid.

Melting point: 189° C.

$R_f$ value: 0.3 (ethyl acetate/methanol 4:1).

$^1$H-NMR (200 MHz, DMSO-$d_6$, δ/ppm): 11.17 (1H, s), 3.67 (2H, dd), 3.32 (partially obscured by the signal for water, 2H, t), 3.21 (2H, t), 2.51 (partially obscured by the signal for DMSO, 2H), 2.25–2.15 (4H, m), 1.93 (2H, quart), 1.78–1.63 (4H, m), 1.62–1.48 (2H, m).

MS (ESI): 605.2 (2M+Na$^+$), 583 (2M+H$^+$), 314 (M+Na$^+$), 292.2 (M+H$^+$).

Example 2

N-[3-(2,4-Dioxo-3,4,7,8-tetrahydro-2H-thiopyrano[4,3-d]pyrimidin-1(5H)-yl)propyl]-N-methylphenylsulphonamide

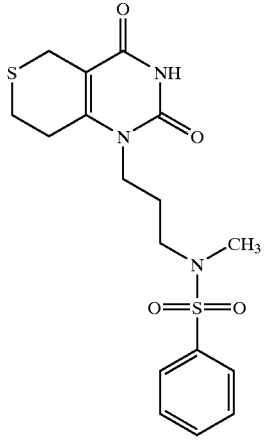

A solution of 0.98 g (4.3 mmol) of N-(3-aminopropyl)-N-methylphenylsulphonamide [preparation according to P. Daetwyler et al., Helv. Chim. Acta, 61, 2646 (1978)], 0.55 g (4.73 mmol) of tetrahydrothiopyran-4-one and a catalytic amount of camphorsulphonic acid in 50 ml of toluene is heated at reflux for 3 hours using a Dean-Stark separator. After cooling to room temperature, the Dean-Stark separator is removed, 0.54 g (5.16 mmol) of chlorocarbonyl isocyanate are added and the mixture is refluxed for another hour. The solvent is removed using a rotary evaporator and the resulting residue is purified by preparative HPLC (RP-C18, acetonitrile/water gradient). This gives 717 mg (42% yield) of an amorphous solid.

$^1$H-NMR (300 MHz, DMSO-$d_6$, δ/ppm): 11.42 (1H, br. s), 7.82–7.58 (5H, m), 3.80–3.70 (2H, m), 3.42 (2H, m), 3.00 (2H, t), 2.92–2.75 (4H, m) 2.68 (3H, s), 1.80–1.65 (2H, s).

MS (DCI): 413.3 (M+NH$_4^+$).

Example 3

N-[3-(2,4-Dioxo-3,4,5,6,7,8-hexahydro-1(2H)-quinazolinyl)cyclohexyl]4-nitrobenzenesulphonamide

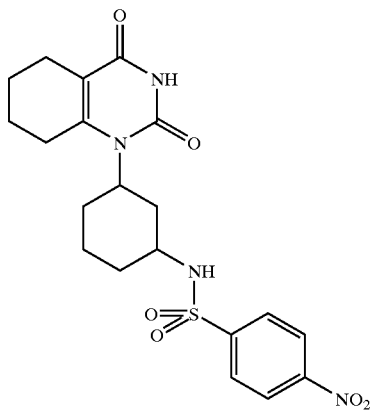

a) tert-butyl 3-(2,4-dioxo-3,4,5,6,7,8-hexahydro-1(2H)-quinazolinyl)cyclo-hexylcarbamate A solution of 2.13 ml (20.53 mmol) of cyclohexanone and 4.0 g (18.66 mmol) of tert-butyl 3-aminocyclohexylcarbamate [prepared from 1,3-diaminocyclohexane and di-tert-butyl dicarbonate {(BOC)$_2$O}] in 300 ml of toluene is treated with a spatula tip of camphorsulphonic acid and boiled for 1.5 hours, with the use of a Dean-Stark separator. The mixture is allowed to cool to room temperature, and 1.8 ml of chlorocarbonyl isocyanate are added. The mixture is again heated at reflux. After 45 minutes, the reaction has ended. Most of the toluene is removed using a rotary evaporator and the residue is diluted with dichloromethane. The mixture is washed with saturated sodium bicarbonate solution and dried over sodium sulphate. The mixture is concentrated using a rotary evaporator and the residue is purified by column chromatography (silica gel, cyclohexane/ethyl acetate 1:2). The product fraction is freed from the solvent and the residue is recrystallized from ethyl acetate. This gives 900 mg (2.48 mmol, 13% yield) of a white solid which is a cis/trans isomer mixture.

Melting point: >240° C.

$R_f$ value: 0.46 (ethyl acetate/methanol 4:1).

$^1$H-NMR (300 MHz, DMSO-d$_6$, δ/ppm): 10.96 (1H, s), 6.81 (1H, d), 3.91–3.79 (1H, m) 3.40–3.24 (1H, m, partially obscured by the signal for water), 2.53–2.47 (2H, m, partially obscured by the signal for DMSO), 2.49–2.24 (2H, m), 2.21 (2H, t), 1.76–1.63 (6H, m), 1.58–1.48 (4H, m), 1.37 (9H, s).

MS (ESI): 749.4 (2M+Na$^+$), 727 (2M+H$^+$), 386.1 (M+Na$^+$), 364 (M+H$^+$).

b) 1-(3-aminocyclohexyl)-5,6,7,8-tetrahydro-2,4(1H,3H)-quinazolinedione hydrochloride A suspension of 860 mg (2.37 mmol) of tert-butyl 3-(2,4-dioxo-3,4,5,6,7,8-hexahydro-1(2H)-quinazolinyl)cyclohexylcarbamate in 6 ml of concentrated hydrochloric acid is heated to 40–50° C. After 2.5 hours, the mixture is, for drying, concentrated using a rotary evaporator. The resulting crude product is recrystallized from ethyl acetate. This gives 700 mg (2.33 mmol, 98% yield) of a colourless solid which is a mixture of cis and trans isomers.

Melting point: >250° C.

$R_f$ value: 0.36 (ethyl acetate/methanol 4:1).

$^1$H-NMR (200 MHz, DMSO-d$_6$, δ/ppm, main isomer): 11.08 (1H, s), 8.08 (3H, s broad), 4.02–3.85 (1H, m), 3.23–3.07 (1H, m), 2.52 (2H, t, partially obscured by the signal for DMSO), 2.20 (2H, t), 1.97–1.84 (2H, m), 1.73–1.62 (6H, m), 1.60–1.48 (4H, m).

MS (ESI): 264 (M–HCl+H$^+$), 247 (M$^+$–HCl–NH$_2$).

c) N-[3-(2,4-dioxo-3,4,5,6,7,8-hexahydro-1(2H)-quinazolinyl)cyclohexyl]-4-nitrobenzenesulphonamide Together with 99 mg (1.25 mmol) of sodium bicarbonate, 150 mg (0.50 mmol) of 1-(3-aminocyclohexyl)-5,6,7,8,-tetrahydro-2,4(1H,3H)-quinazolinedione hydrochloride in 10 ml of water, to which a few drops of 2-molar sodium carbonate solution have been added, are heated to 50° C. This solution is treated with 166 mg (0.75 mmol) of 4-nitrobenzenesulphonyl chloride. After a couple of minutes, a wax-like precipitate is formed. After one hour, the mixture is acidified with dilute hydrochloric acid and extracted with dichloromethane. The organic phase is concentrated and the resulting residue is recrystallized from ethyl acetate. This gives 33 mg (0.07 mmol) of a white solid.

Melting point: >240° C.

$R_f$ value: 0.77 (ethyl acetate/methanol 4:1).

$^1$H-NMR (200 MHz, DMSO-d$_6$, δ/ppm, main isomer): 10.99 (1H, s), 8.42 (2H, d), 8.16 (1H, d), 8.07 (2H, d), 3.90–3.73 (1H, m) 3.31–3.13 (1H, m), 2.45–2.08 (6H, m), 1.70–1.42 (8H, m), 1.30–0.95 (2H, m).

MS (ESI): 897.5 (2H+H$^+$), 490.3 (M+H$^+$+CH$_3$CN), 449.3 (M+H$^+$).

Example 4

N-[3-(2,4-Dioxo-3,4,5,6,7,8-hexahydro-1(2H)-quinazolinyl)propyl]-4-fluoro-N-methylphenylsulphonamide

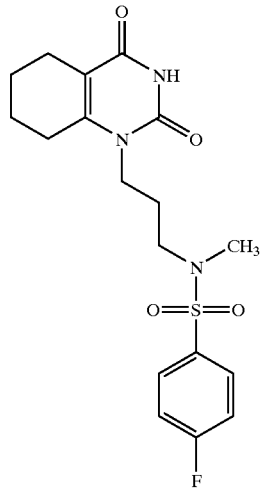

a) 1-{3-[benzyl(methyl)amino]propyl}-5,6,7,8-tetrahydro-2,4(1H, 3H)-quinazolinedione A solution of 24.0 g (134.6 mmol) of N-(3-aminopropyl)-N-benzyl-N-methylamine [J.-M. Contreras et al., J. Med. Chem. 42, 730 (1999)] and 14.5 g (148.1 mmol) of cyclohexanone in 200 ml of toluene is heated at reflux for two hours using a Dean-Stark separator. The mixture is then allowed to cool to room temperature and treated with 17.0 g (161.6 mmol) of chlorocarbonyl isocyanate. A precipitate is formed. The mixture is once more heated at reflux. After two hours, the reaction has ended. The mixture is diluted with ethyl acetate and washed with saturated sodium bicarbonate solution and dried over sodium sulphate. The solvent is removed and the residue is purified by column chromatography (silica gel, ethyl acetate). This gives 22.5 g (68.7 mmol, 51% yield) of a yellowish oil.

$R_f$ value: 0.3 (ethyl acetate/methanol 4:1).

$^1$H-NMR (200 MHz, DMSO-d$_6$, δ/ppm): 11.06 (1H, s), 7.37–7.19 (5H, m), 3.86 (2H, dd), 3.45 (2H, s), 2.60–2.50 (2H, m, partially obscured by the signal for DMSO), 2.35 (2H, t), 2.20 (2H, t), 2.07 (3H, s), 1.80–1.48 (6H, m).

MS (ESI): 328 (M+H$^+$).

b) 1-[3-(methylamino)propyl]-5,6,7,8-tetrahydro-2,4(1H, 3H)-quinazolinedione

A solution of 4.29 g (13.11 mmol) of 1-{3-[benzyl(methyl)amino]propyl}-5,6,7,8-tetrahydro-2,4(1H,3H)-quinazolinedione in a mixture of 50 ml of methanol and 10 ml of tetrahydrofuran is admixed with 5.6 mg of 10% palladium-on-carbon. Over a period of 45 minutes, three portions of in total 8.61 g (136.6 mmol) of ammonium formate are then added. After the addition has ended, the mixture is heated at reflux for 1.5 hours. After cooling, the mixture if filtered through a little kieselguhr and the solvent is removed under reduced pressure. This gives 2.24 g (9.44 mmol, 72% yield) of the product as a colourless solid.

$^1$H-NMR (200 MHz, DMSO-$d_6$, δ/ppm): 11.26 (1H, s), 8.95 (1H, br. s), 2.89 (2H, t), 3.82 (2H, t), 2.65–2.42 (5H, m), 2.20–2.12 (2H, m), 2.00–1.50 (6H, m).

MS (ESI): 238.1 (M+H$^+$).

c) N-[3-(2,4-dioxo-3,4,5,6,7,8-hexahydro-1(2H)-quinazolinyl)propyl]-4-fluoro-N-methylphenylsulphonamide A solution of 75 mg (0.32 mmol) of 1-[3-(methylamino)propyl]-5,6,7,8-tetrahydro-2,4(1H,3H)-quinazolinedione and 61.5 mg (0.32 mmol) of 4-fluorophenylsulphonyl chloride in 3 ml of pyridine is stirred at room temperature overnight. The reaction mixture is then adjusted to pH 1 using 2-molar hydrochloric acid and extracted twice with in each case 20 ml of ethyl acetate. The organic phase is concentrated under reduced pressure and the resulting residue is purified by preparative HPLC (RP-C18, acetonitrile/water gradient). This gives 43.1 mg (34% yield) of the product as an amorphous solid.

$^1$H-NMR (300 MHz, DMSO-$d_6$, δ/ppm): 11.20 (1H, s), 7.89–7.81 (2H, m), 7.52–7.42 (2H, m), 3.71 (2H, m), 2.98 (2H, t), 2.69 (3H, s), 2.65–2.48 (2H, m), 1.50–1.61 (2H, m), 2.20 (2H, t), 1.80–1.86 (4H, m).

MS (CI): 413.3 (M+NH$_4^+$).

Example 5

2,2,2-Trichloroethyl 3-(2,4-dioxo-3,4,7,8-tetrahydro-2H-thiopyrano[4,3-d]pyrimidin-1(5H)-yl)propyl(methyl)carbamate

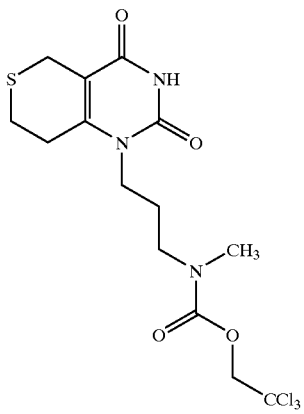

a) 1-{3-[benzyl(methyl)amino]propyl}-1,5,7,8-tetrahydro-2H-thiopyrano[4,3-d]pyrimidine-2,4(3H)-dione A solution of 9.9 g (55.55 mmol) of N-(3-aminopropyl)-N-benzyl-N-methylamine and 7.1 g (61.11 mmol) of tetrahydro-4H-thiopyran-4-one in 250 ml of toluene is treated with a spatula tip of camphorsulphonic acid, and the mixture is heated at reflux for two hours using a Dean-Stark separator. The mixture is then allowed to cool to room temperature, and 7.0 g (66.67 mmol) of chlorocarbonyl isocyante are added. A precipitate is formed. The mixture is once more heated at reflux. After 30 minutes, the reaction has ended. The mixture is diluted with dichloromethane and washed with saturated sodium bicarbonate solution and dried over sodium sulphate. The solvent is then removed and the residue is purified by column chromatography (silica gel, ethyl acetate). This gives 12.8 g (37 mmol, 67% yield) of a yellowish material which solidifies like a glass.

R$_f$ value: 0.42 (ethyl acetate/methanol 4:1).

$^1$H-NMR (200 MHz, DMSO-$d_6$, δ/ppm): 11.49 (1H, s), 7.37–7.20 (5H, m), 3.79 (2H, dd), 3.45 (2H, s), 3.36 (2H, s), 2.83 (4H, s), 2.37 (2H, t), 2.10 (3H, s), 1.80–1.67 (2H, m).

MS (ESI): 346 (M+H$^+$).

b) 2,2,2-trichloroethyl 3-(2,4-dioxo-3,4,7,8-tetrahydro-2H-thiopyrano-[4,3-d]pyrimidin-1-(5H)-yl)propyl(methyl)carbamate A solution of 11.5 g (33.29 mmol) of 1-{3-[benzyl(methyl)amino]propyl}-1,5,7,8-tetrahydro-2H-thiopyrano[4,3-d]pyrimidine-2,4-(3H)-dione in 200 ml of acetonitrile is treated with 7.92 g (36.63 mmol) of 2,2,2-trichloroethyl chloroformate, and the mixture is stirred at room temperature for 30 minutes. The solvent is then removed under reduced pressure and the residue is purified by column chromatography (silica gel, cyclohexane/ethyl acetate 1:1). This gives 9.4 g (63% yield) of a colourless solid.

$^1$H-NMR (200 MHz, DMSO-$d_6$, δ/ppm): 11.40 (1H, s), 4.85–4.78 (2H, m), 3.85–3.70 (2H, m), 3.35 (3H, s), 2.98–2.80 (8H, m), 1.90–1.72 (2H, m).

MS (CI): 447 (M+NH$_4^+$).

Example 6

N-[3-(2,4-Dioxo-3,4,7,8-tetrahydro-2H-thiopyran[4,3-d]pyrimidin-1(5H)-yl)propyl]-N-methyl-2,1,3-benzothiadiazole-4-sulphonamide

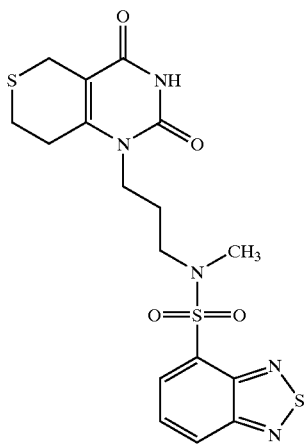

a) 1-[3-(methyl)amino]propyl]-1,5,7,8-tetrahydro-2H-thiopyrano[4,3-d]pyrimidine-2,4(3H)-dione hydrochloride A solution of 3.0 g (6.96 mmol) of 2,2,2-trichloroethyl 3-(2,4-dioxo-3,4,7,8-tetrahydro-2H-thiopyrano[4,3-d]pyrimidin-1-(5H)-yl)propyl(methyl)carbamate in 60 ml of tetrahydrofuran is treated with 60 ml of 0.01-molar hydrochloric acid and 2.28 g (34.8 mmol) of zinc dust. Over a period of four hours, a total of 4 ml of 2-molar hydrochloric acid and 455 mg (6.96 mmol) of zinc dust are added in portions. After the reaction has gone to completion, the mixture is concentrated under reduced pressure, diluted with 60 ml of 0.01-molar hydrochloric acid and washed with ethyl acetate. The aqueous phase is evaporated to dryness and used for the next step without further purification.

$^1$H-NMR (200 MHz, DMSO-$d_6$, δ/ppm): 11.49 (1H, s), 8.30 (2H, br. s), 4.00–4.12 (4H, m), 3.82 (2H, t), 2.80–3.00 (4H, m), 2.57 (3H, t), 1.92–1.78 (2H, m).

MS (ESI+): 456.4 (M−HCl+H$^+$).

b) N-[3-(2,4-dioxo-3,4,7,8-tetrahydro-2H-thiopyran[4,3-d]pyrimidin-1(5H)-yl)propyl]-N-methyl-2,1,3-benzothiadiazole-4-sulphonamide A solution of 150 mg (0.59 mmol) of 1-[3-(methylamino)propyl]-1,5,7,8-tetrahydro-2H-thiopyrano[4,3-d]pyrimidine-2,4(3H)-dione hydrochloride and 2.4 ml of pyridine is treated with 206.8 mg (0.88 mmol) of benzothiadiazole-4-sulphonyl chloride, 0.6 ml (4.3 mmol) of triethylamine and a spatula tip of 4-(N,N-dimethylamino)pyridine. The mixture is stirred at room temperature overnight and then concentrated to dryness using a rotary evaporator, and the product is isolated by preparative HPLC (RP-C18, acetonitrile/water gradient). This gives 104.5 mg (0.23 mmol, 39% yield) of an amorphous solid.

$^1$H-NMR (300 MHz, DMSO-$d_6$, δ/ppm): 11.40 (1H, br. s), 8.46–8.18 (2H, m), 7.92–7.82 (1H, m), 3.85–3.69 (2H, m), 3.40–3.23 (4H, m), 2.75–2.90 (7H, m), 1.85–1.65 (2H, m).

MS (ESI+): 454 (M+H$^+$).

Example 106

N-[3-(2,4-Dioxo-3,4,5,6,7,8-hexahydro-1(2H)-quinazolinyl)propyl]-N-methyl-5-(2-pyrazinyl)-2-thiophenesulphonamide

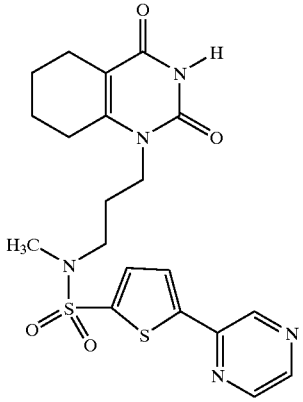

Under argon, 186.8 mg (0.51 mmol) of 2-tributylstannylpyrazine and 27.3 mg (0.039 mmol) of bis(triphenylphosphine)palladium(II) chloride are added to a solution of 200 mg (0.39 mmol) of the compound from Example 44 in dimethylformamide (5 ml). The reaction mixture is stirred at 120° C. overnight and, after cooling, purified by preparative HPLC (RP-C18, acetonitrile/water gradient). This gives 42 mg of the product (23%) as an amorphous solid.

$^1$H-NMR (200 MHz, DMSO-$d_6$, δ/ppm): 11.20 (1H, br. s), 9.38 (1H, d), 8.63–8.69 (2H, m), 8.13 (1H, d), 7.75 (1H, d), 3.68–3,81 (2H, m), 3.02–3.15 (2H, m), 2.78 (3H, s), 2.45–2.60 (2H, obscured by the signal for DMSO), 2.11–2.27 (2H, m), 1.45–1.90 (6H, m).

MS (ESI+): 462.3 (M+H$^+$).

Example 107

N-[3-(2,4-Dioxo-3,4,5,6,7,8-hexahydro-1(2H)-quinazolinyl)propyl]-5-(4-formylphenyl)-N-methyl-2-thiophenesulphonamide

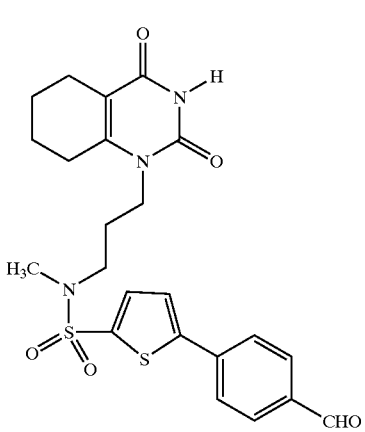

Under argon, 500 mg (1.08 mmol) of the compound from Example 44 and 210 mg (1.41 mmol) of 4-formylphenylboronic acid are added to a solution of 75.9 mg (0.11 mmol) of bis(triphenylphosphine)palladium(II) chloride in DMF (5 ml), and the mixture is stirred at 70° C. for 1 h. 0.7 ml of aqueous sodium carbonate solution (2M) are then added and the reaction mixture is stirred at 100° C. overnight. After cooling, the reaction mixture is purified directly by preparative HPLC (RP-C18, acetonitrile/water gradient). This gives 418 mg of the product (79%) as an amorphous solid.

$^1$H-NMR (200 MHz, DMSO-$d_6$, δ/ppm): 11.20 (1H, br. s), 7.96–8.05 (5H, m), 7.88 (1H, d), 7.72 (1H, d), 3.65–3,82 (2H, m), 3.00–3.15 (2H, m), 2.79 (3H, s), 2.47–2.62 (2H, obscured by the signal for DMSO), 2.13–2.27 (2H, m), 1.46–1.90 (6H, m). MS (ESI+): 488.1 (M+H$^+$).

Example 108

N-[3-(2,4-Dioxo-3,4,5,6,7,8-hexahydro-1(2H)-quinazolinyl)propyl]-5-{4-[(E)-(hydroxylimine)methyl]phenyl}-N-methyl-2-thiophenesulphonamide

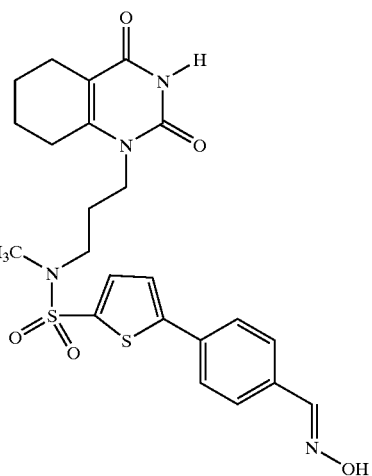

33.8 mg (1.03 mmol) of N-hydroxylamine hydrochloride and 84.1 mg (1.03 mmol) of sodium acetate are added to a solution of 100 mg (0.21 mmol) of the compound from Example 107 in tetrahydrofuran/water (20 ml, 1:1 mixture), and the mixture is heated at reflux for 3 h. Another 33.8 mg (1.03 mmol) of N-hydroxylamine hydrochloride and 84.1 mg (1.03 mmol) of sodium acetate are then added, and the mixture is stirred at reflux overnight. After cooling, the organic solvent is evaporated under reduced pressure and the resulting precipitate is filtered and washed with water and diethyl ether. Further purification is carried out using preparative HPLC (RP-C18, acetonitrile/water gradient). This gives 32 mg of the product (31%) as an amorphous solid.

$^1$H-NMR (200 MHz, DMSO-$d_6$, δ/ppm): 11.40 (1H, s), 11.20 (1H, s), 8.19 (1H, s), 7.63–7.85 (6H, m), 3.68–3.82 (2H, m), 3.01–3.14 (2H, m), 2.78 (3H, s), 2.46–2.62 (2H, obscured by the signal for DMSO), 2.12–2.26 (2H, m), 1.46–1.90 (6H, m).

MS (ESI+): 503.1 (M+H$^+$).

Example 109

4-{[[3-(2,4,-Dioxo-3,4,7,8-tetrahydro-2H-thiopyran[4,3-d]pyrimidin-1(5H)-yl)propyl](methyl)amino]sulphonyl}-N'-hydroxy-4-phenylcarboxamidine

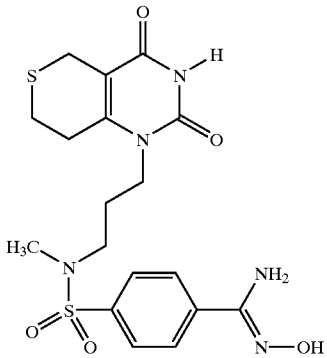

Triethylamine (0.152 ml, 1.09 mmol) is added dropwise to a suspension of 200 mg (0.48 mmol) of the compound from Example 71 and 72.7 mg (1.05 mmol) of hydroxylammonium hydrochloride in ethanol (10 ml), and the reaction mixture is stirred at 75° C. for 6 hours. The ethanol is evaporated under reduced pressure and the solid is then taken up in a little water, filtered and washed with diethyl ether. This gives 186 mg of the product (82%) as an amorphous solid.

$^1$H-NMR (200 MHz, DMSO-$d_6$, δ/ppm): 11.39 (1H, br. s), 9.97 (1H, s), 7.90 (2H, d), 7.74 (2H, d), 5.98 (2H, s), 3.69–3.82 (2H, m), 3.35 (2H, s), 2.95–3.07 (2H, m), 2.77–2.91 (4H, m), 2.69 (3H, s), 1.69–1.81 (2H, m).

MS (ESI+): 454 (M+H$^+$).

Example 110

4-{[[3-(2,4,-Dioxo-3,4,7,8-tetrahydro-2H-thiopyran[4,3-d]pyrimidin-1(5H)-yl)propyl](methyl)amino]sulphonyl}-4-phenylcarboxamidinium*hydrochloride

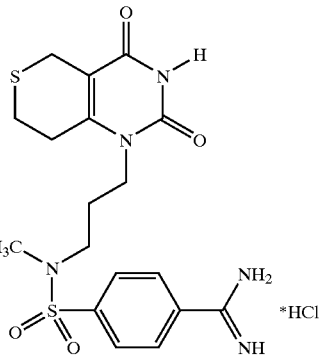

Under argon, palladium-on-carbon (10% by weight of Pd, 40 mg) is added to a solution of 350 mg (0.695 mmol) of the compound from Example 109 in glacial acetic acid (21 ml) and acetic anhydride (78 mg, 0.76 mmol), and the mixture is hydrogenated under an atmosphere of hydrogen (atmospheric pressure) at room temperature for 48 h. The reaction mixture is filtered through Celite, the filter residue is washed with methanol and the solvent is removed under reduced pressure. The residue is separated by column chromatography on Florisil (mobile phase: dichloromethane/methanol) and then purified by preparative HPLC (RP-C18, acetonitrile/0.2% aqueous HCl gradient). This gives 17 mg of the product (5%) as an amorphous solid.

$^1$H-NMR (200 MHz, DMSO-$d_6$, δ/ppm): 11.45 (1H, br. s), 9.54 (2H, br. s), 9.25 (2H, br. s), 8.01 (4H, m), 3.70–3,84 (2H, m), 3.00–3.13 (2H, m), 2.80–2.94 (4H, m), 2.74 (3H, s), 2.46–2.58 (2H, obscured by the signal for DMSO), 1.68–1.88 (2H, m).

MS (ESI+): 438.1 (M–HCl+H$^+$).

The compounds 7 to 105 listed in the table below are prepared in a similar manner:

| Example No. | Structure | Rt [min] [a] | MS [M + H]$^+$ | Rf value [b] | m.p. [° C.] |
|---|---|---|---|---|---|
| 7 | 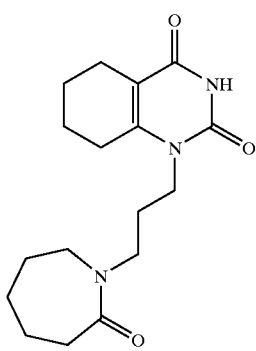 | | | 0.6 (E) | |

-continued

| Example No. | Structure | Rt [min] [a] | MS [M + H]⁺ | Rf value [b] | m.p. [° C.] |
|---|---|---|---|---|---|
| 8 | 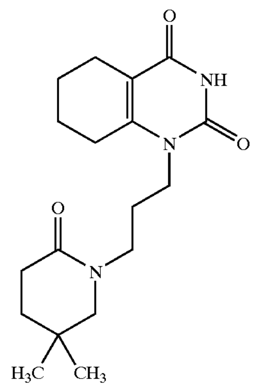 | | | 0.6 (E) | |
| 9 | 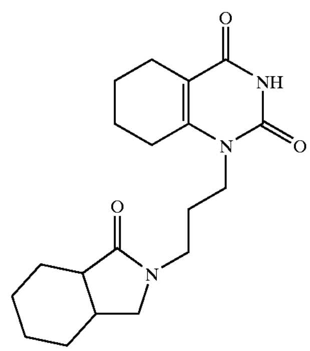 | | | 0.7 (E) | |
| 10 | 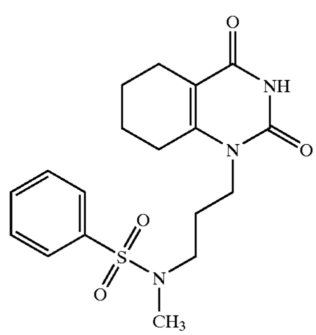 | 3.88 (A) | 378.5 | | |
| 11 | 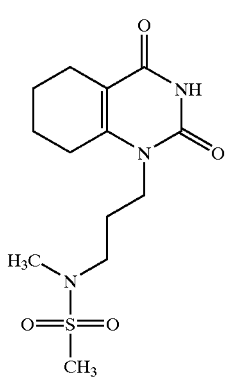 | 2.43 (C) | 316.2 | | |

-continued
| Example No. | Structure | Rt [min] [a] | MS [M + H]+ | Rf value [b] | m.p. [° C.] |
|---|---|---|---|---|---|
| 12 | 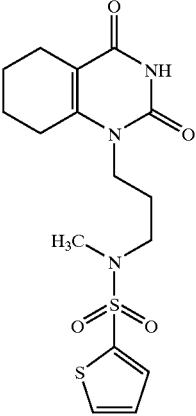 | 3.32 (C) | 384.1 | | |
| 13 | 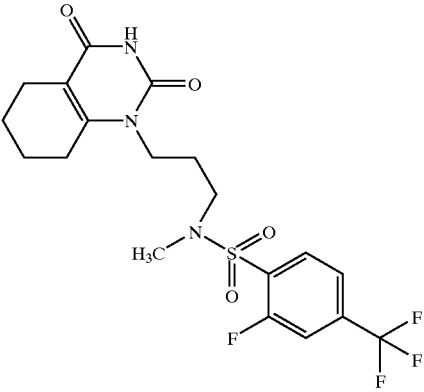 | 3.99 (C) | 464.3 | | |
| 14 | 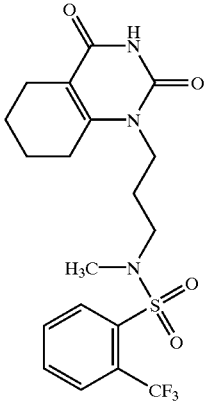 | 4.18 (C) | 446.3 | | |

-continued

| Example No. | Structure | Rt [min] [a] | MS [M + H]+ | Rf value [b] | m.p. [° C.] |
|---|---|---|---|---|---|
| 15 | 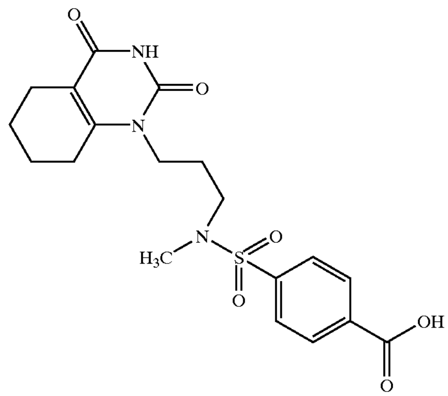 | 3.11 (C) | 422.3 | | |
| 16 | 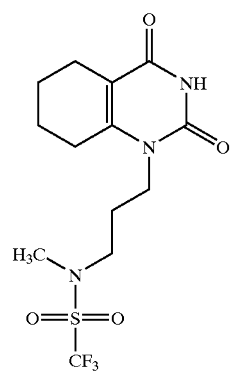 | 3.59 (C) | 370.1 | | |
| 17 | 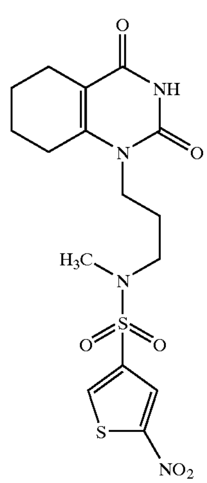 | 3.51 (C) | 429.1 | | |

-continued

| Example No. | Structure | Rt [min] [a] | MS [M + H]+ | Rf value [b] | m.p. [° C.] |
|---|---|---|---|---|---|
| 18 | 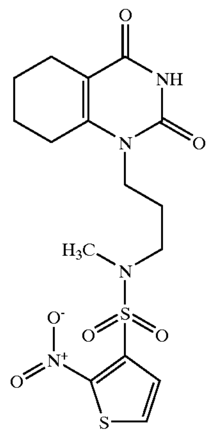 | 3.66 (C) | 429.1 | | |
| 19 | 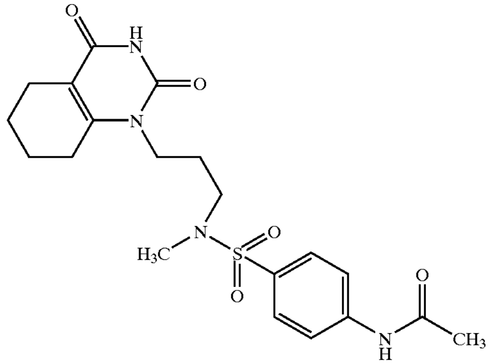 | 3.03 (C) | 435.4 | | |
| 20 | 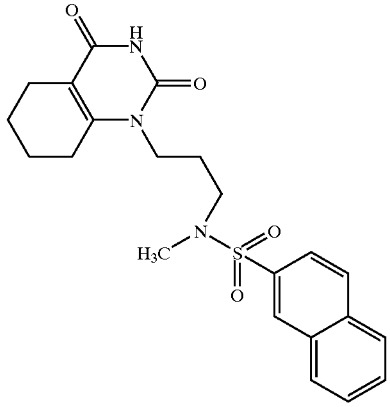 | 3.86 (C) | 428.4 | | |

-continued

| Example No. | Structure | Rt [min] [a] | MS [M + H]+ | Rf value [b] | m.p. [° C.] |
|---|---|---|---|---|---|
| 21 | 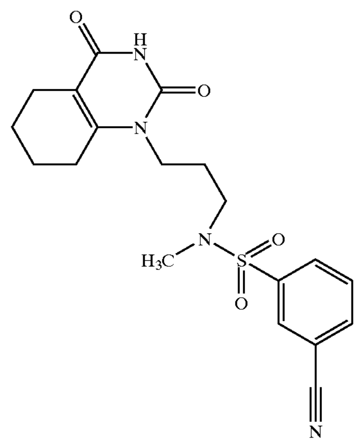 | 3.39 (C) | 403.3 | | |
| 22 | 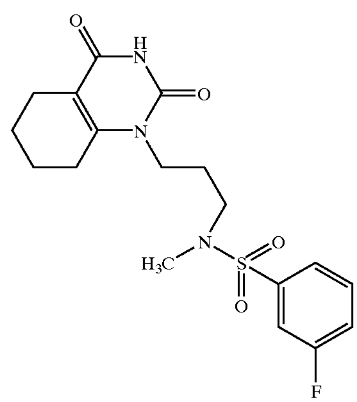 | 3.53 (C) | 396.3 | | |
| 23 | 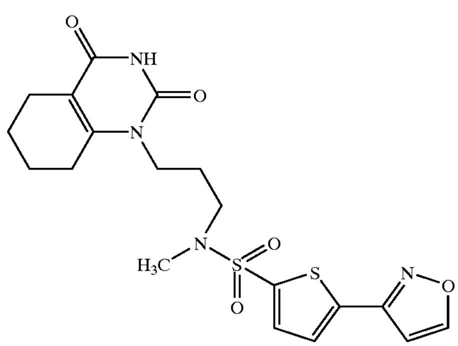 | 3.57 (C) | 451.3 | | |
| 24 | 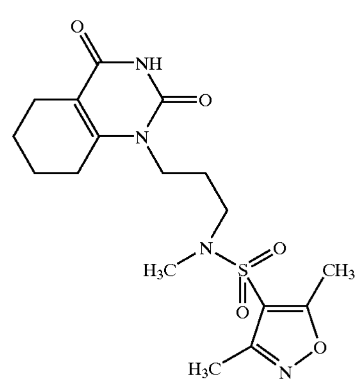 | 3.33 (C) | 397.3 | | |

-continued

| Example No. | Structure | Rt [min] [a] | MS [M + H]⁺ | Rf value [b] | m.p. [° C.] |
|---|---|---|---|---|---|
| 25 | 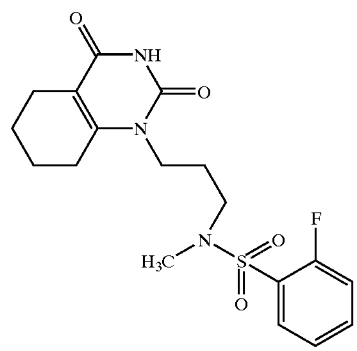 | 3.44 (C) | 396.3 | | |
| 26 | 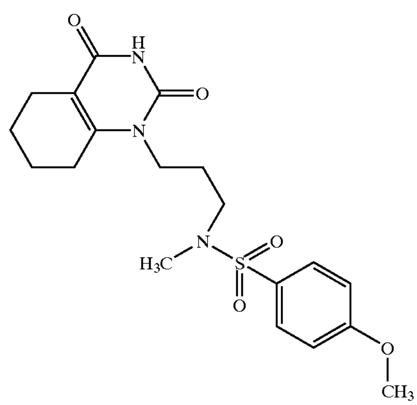 | 3.46 (C) | 408.4 | | |
| 27 | 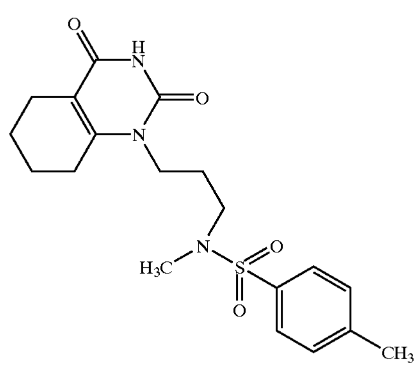 | 3.61 (C) | 392.4 | | |
| 28 | 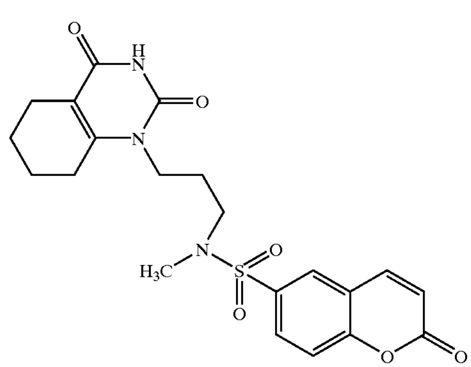 | 3.29 (C) | 446.3 | | |

-continued
| Example No. | Structure | Rt [min] [a] | MS [M + H]+ | Rf value [b] | m.p. [° C.] |
|---|---|---|---|---|---|
| 29 | 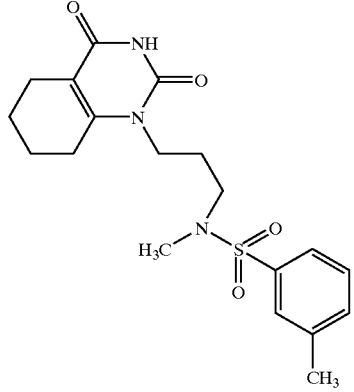 | 3.62 (C) | 392.4 | | |
| 30 | 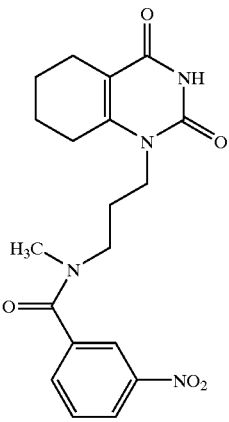 | 3.01 (C) | 387.2 | | |
| 31 | 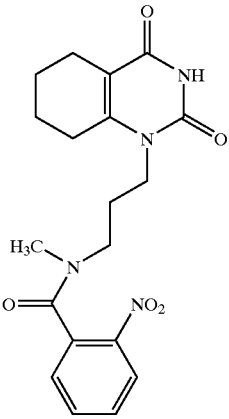 | 3.01 (C) | 387.2 | | |

-continued

| Example No. | Structure | Rt [min] [a] | MS [M + H]+ | Rf value [b] | m.p. [° C.] |
|---|---|---|---|---|---|
| 32 | 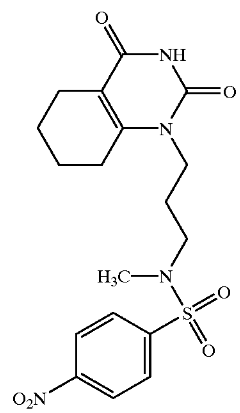 | 4.06 (A) | 423.2 | | |
| 33 | 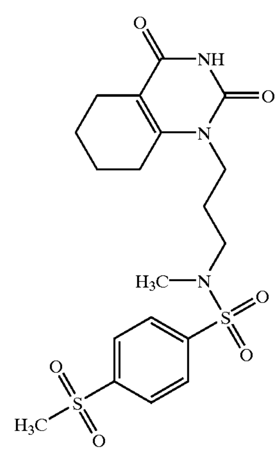 | 3.74 (A) | 456.3 | | |
| 34 | 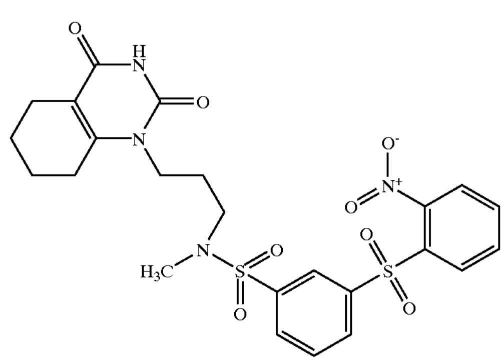 | 3.76 (C) | 563.2 | | |

-continued

| Example No. | Structure | Rt [min] [a] | MS [M + H]+ | Rf value [b] | m.p. [° C.] |
|---|---|---|---|---|---|
| 35 | 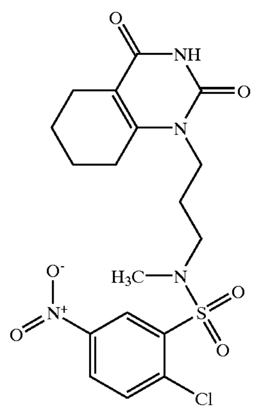 | 3.67 (C) | 457.2 | | |
| 36 | 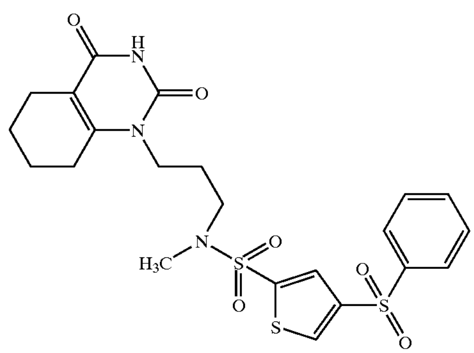 | 4.87 (D) | 524.2 | | |
| 37 | 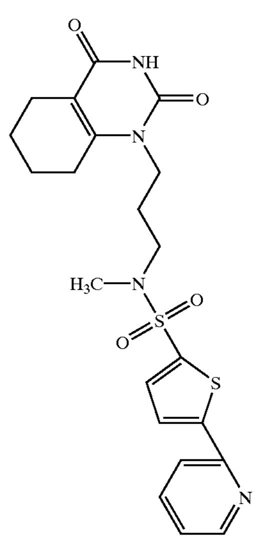 | 4.79 (D) | 461.2 | | |

-continued

| Example No. | Structure | Rt [min] [a] | MS [M + H]+ | Rf value [b] | m.p. [° C.] |
|---|---|---|---|---|---|
| 38 | 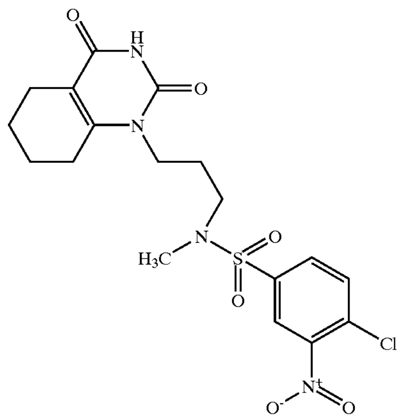 | 4.93 (D) | 457.1 | | |
| 39 | 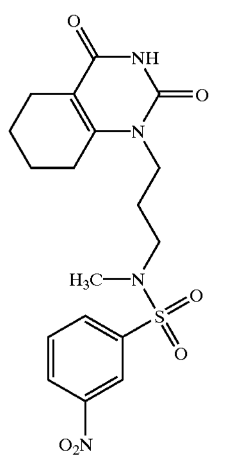 | 3.99 (A) | 423.2 | | |
| 40 | 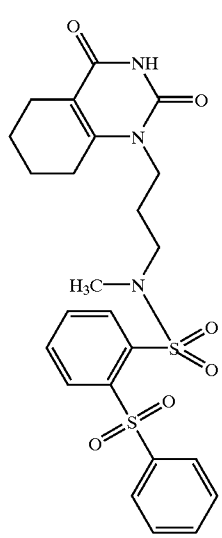 | 3.58 (C) | 518.2 | | |

-continued
| Example No. | Structure | Rt [min] [a] | MS [M + H]+ | Rf value [b] | m.p. [° C.] |
|---|---|---|---|---|---|
| 41 | 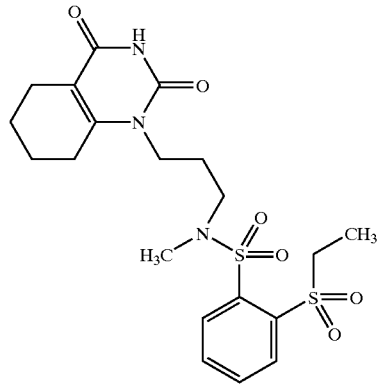 | 3.83 (A) | 470.3 | | |
| 42 | 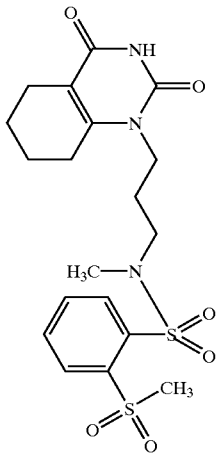 | 3.70 (A) | 456.3 | | |
| 43 | 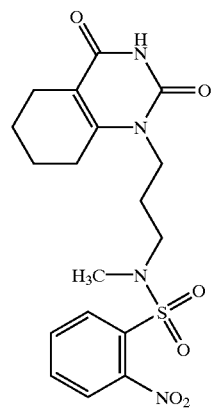 | 3.46 (C) | 423.1 | | |

-continued
| Example No. | Structure | Rt [min] [a] | MS [M + H]+ | Rf value [b] | m.p. [° C.] |
|---|---|---|---|---|---|
| 44 | 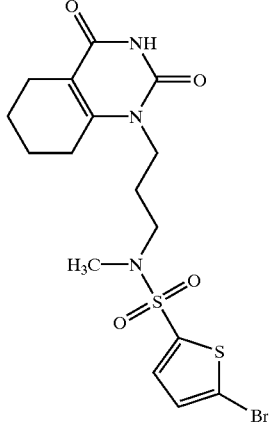 | 3.80 (C) | 464 | | |
| 45 | 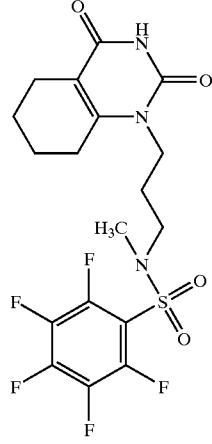 | 3.91 (C) | 468.1 | | |
| 46 | 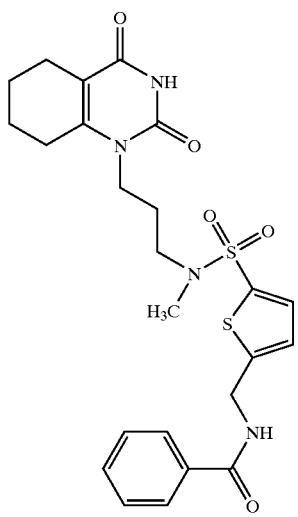 | 3.50 (C) | 517.2 | | |

-continued

| Example No. | Structure | Rt [min] [a] | MS [M + H]+ | Rf value [b] | m.p. [° C.] |
| --- | --- | --- | --- | --- | --- |
| 47 | 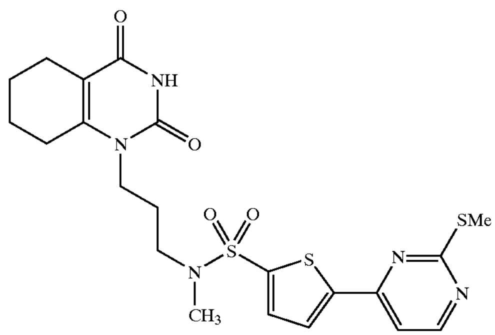 | 3.89 (C) | 508.1 | | |
| 48 | 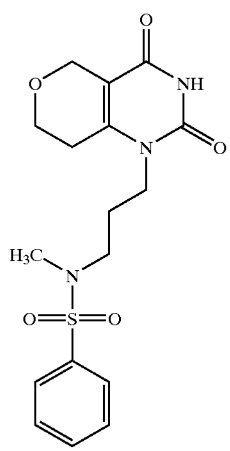 | 3.57 (A) | 380.3 | | |
| 49 | 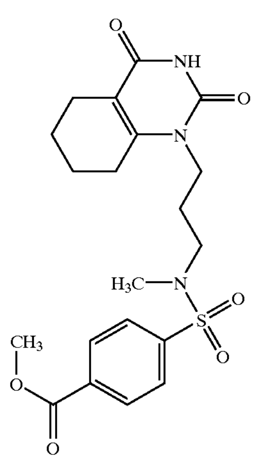 | 3.51 (C) | 436.2 | | |

-continued

| Example No. | Structure | Rt [min] [a] | MS [M + H]+ | Rf value [b] | m.p. [° C.] |
|---|---|---|---|---|---|
| 50 | 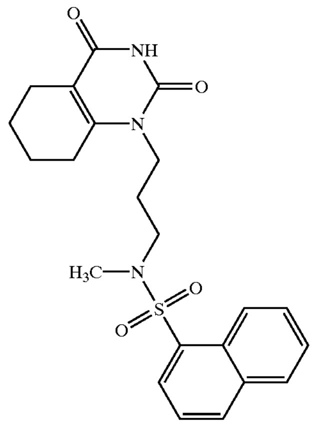 | 4.18 (A) | 428 | | |
| 51 | 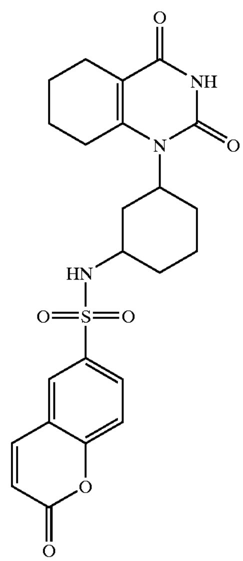 | | | 0.72 (E) | >240 |
| 52 | 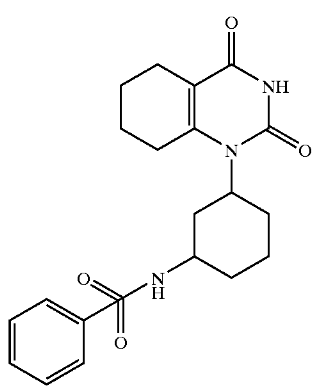 | | | 0.71 (E) | >240 |

-continued

| Example No. | Structure | Rt [min] [a] | MS [M + H]+ | Rf value [b] | m.p. [° C.] |
|---|---|---|---|---|---|
| 53 | 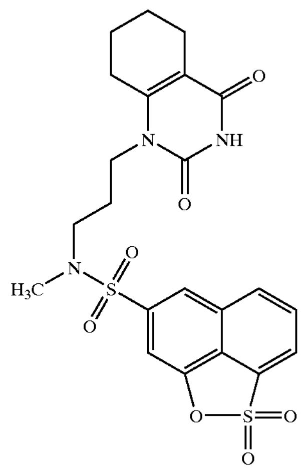 | 4.21 (A) | 506 | | |
| 54 | 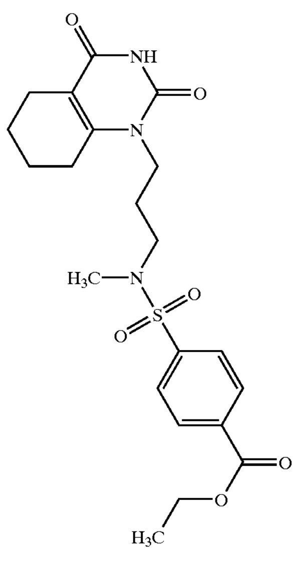 | 3.75 (C) | 430.4 | | |
| 55 | 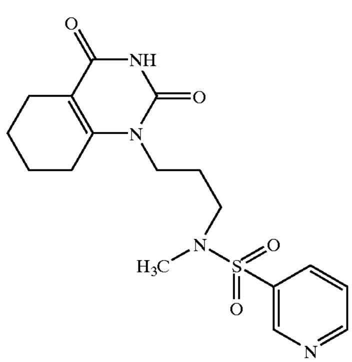 | 2.91 (C) | 379.1 | | |

-continued
| Example No. | Structure | Rt [min] [a] | MS [M + H]+ | Rf value [b] | m.p. [° C.] |
|---|---|---|---|---|---|
| 56 | 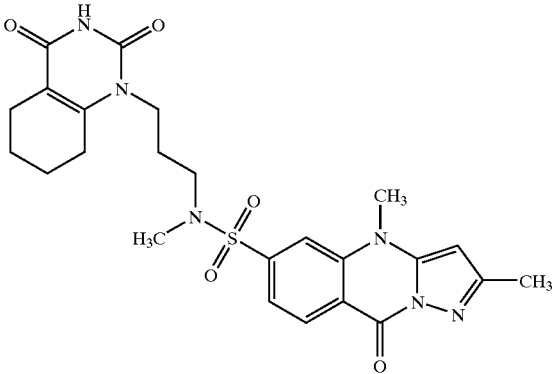 | 3.10 (C) | 513.2 | | |
| 57 | 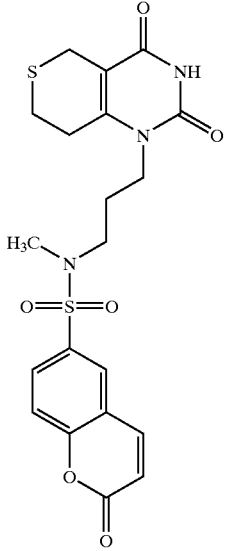 | 3.14 (C) | 464.1 | | |
| 58 | 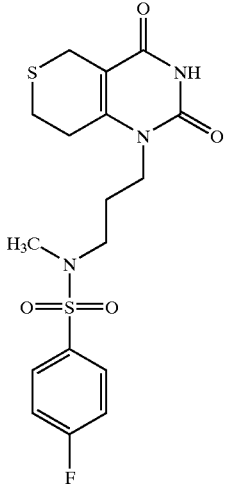 | 3.43 (C) | 414.2 | | |

-continued

| Example No. | Structure | Rt [min] [a] | MS [M + H]+ | Rf value [b] | m.p. [° C.] |
|---|---|---|---|---|---|
| 59 | 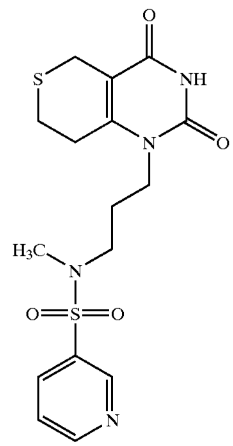 | 2.80 (C) | 397.2 | | |
| 60 | 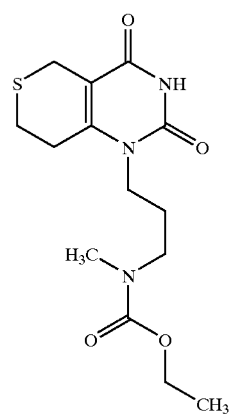 | 3.48 (A) | 328.2 [M + NH4]+ | | |
| 61 | 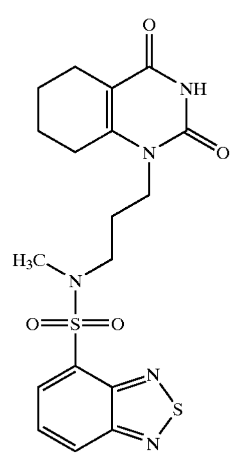 | | | 0.28 (F) | 170 |

-continued

| Example No. | Structure | Rt [min] [a] | MS [M + H]+ | Rf value [b] | m.p. [° C.] |
|---|---|---|---|---|---|
| 62 | 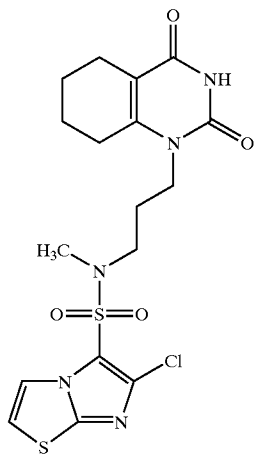 | | | 0.57 (E) | >240 |
| 63 | 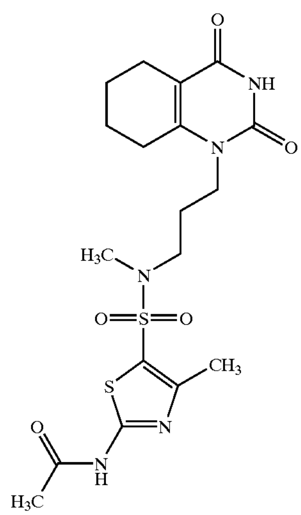 | | | 0.5 (E) | >240 |
| 64 | 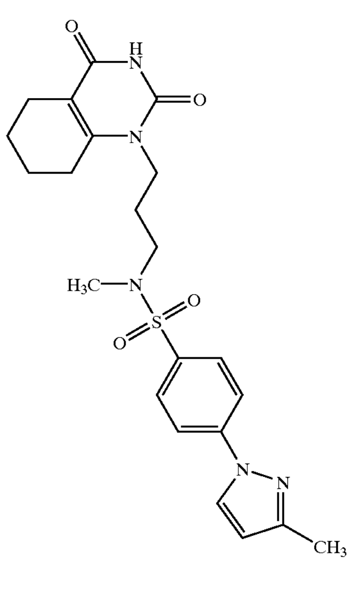 | 3.64 (C) | 458.4 | | |

-continued

| Example No. | Structure | Rt [min] [a] | MS [M + H]+ | Rf value [b] | m.p. [° C.] |
|---|---|---|---|---|---|
| 65 | 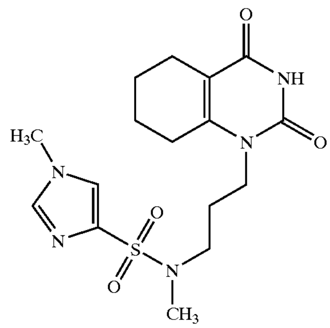 | | | 0.28 (E) | 128 |
| 66 | 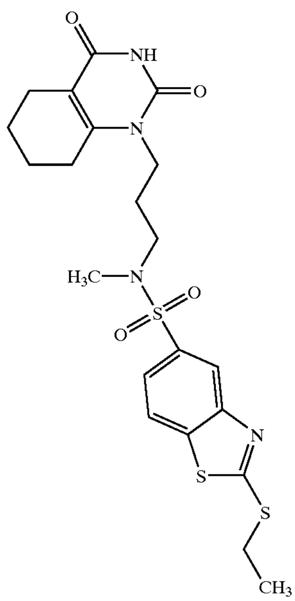 | 4.08 (C) | 495.4 | | |
| 67 | 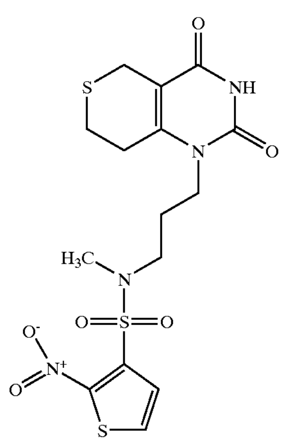 | 3.47 (C) | 447 | | |

-continued

| Example No. | Structure | Rt [min] [a] | MS [M + H]+ | Rf value [b] | m.p. [° C.] |
|---|---|---|---|---|---|
| 68 | 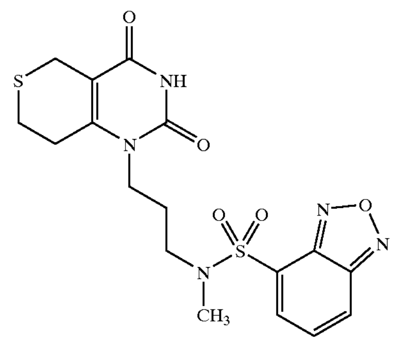 | 4.48 (D) | 438.1 | | |
| 69 | 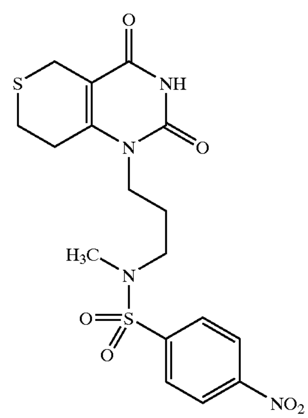 | 3.48 (C) | 441.1 | | |
| 70 | 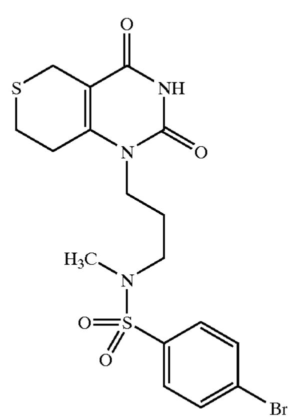 | 3.67 (C) | 474 [M − H]− | | |

-continued

| Example No. | Structure | Rt [min] [a] | MS [M + H]+ | Rf value [b] | m.p. [° C.] |
|---|---|---|---|---|---|
| 71 | 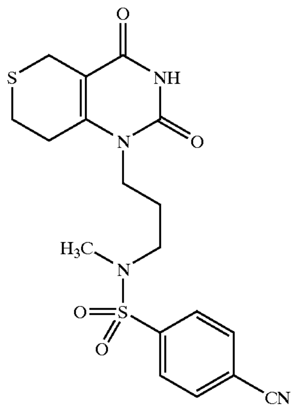 | 3.33 (C) | 421.1 | | |
| 72 | 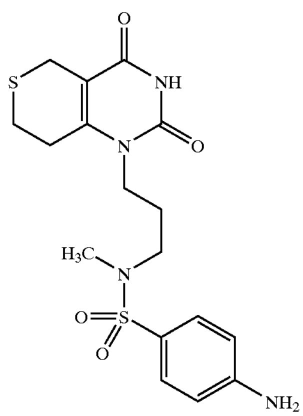 | 2.89 (C) | 411.1 | | |
| 73 | 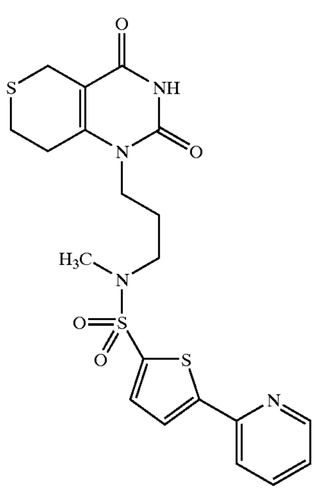 | 3.60 (C) | 479.2 | | |

-continued

| Example No. | Structure | Rt [min] [a] | MS [M + H]+ | Rf value [b] | m.p. [° C.] |
|---|---|---|---|---|---|
| 74 | 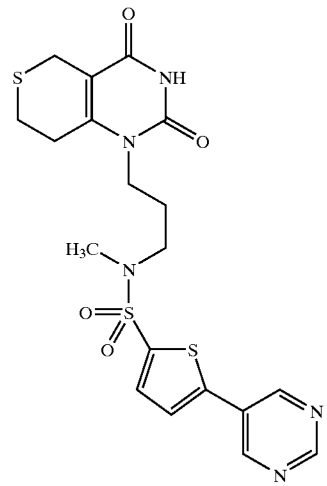 | 3.71 (C) | 478.1 [M − H]− | | |
| 75 | 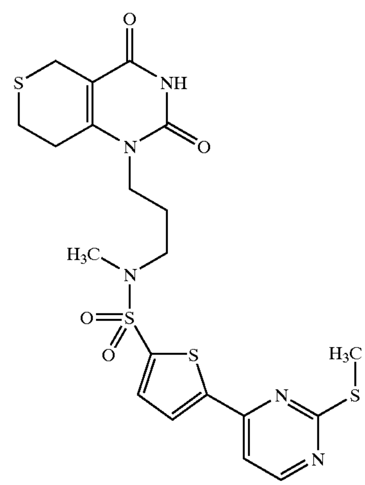 | 3.80 (C) | 526.1 | | |
| 76 | 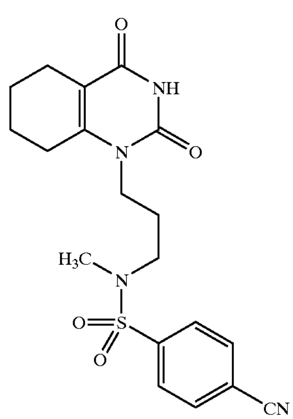 | 3.35 (C) | 403.1 | | |

-continued

| Example No. | Structure | Rt [min] [a] | MS [M + H]+ | Rf value [b] | m.p. [° C.] |
| --- | --- | --- | --- | --- | --- |
| 77 | 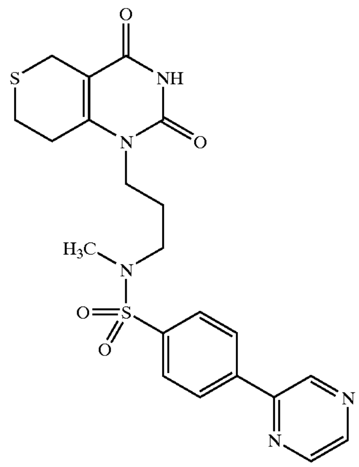 | 3.86 (C) | 474 | | |
| 78 | 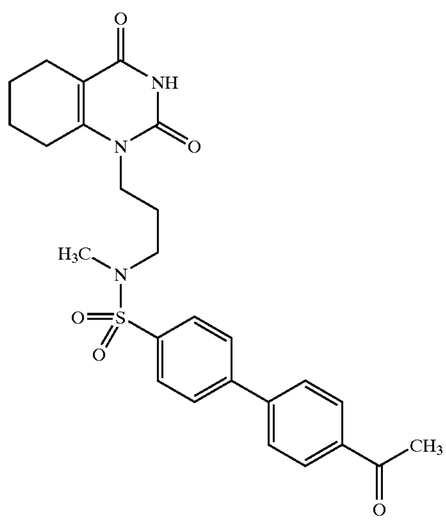 | 4.24 (A) | 496 | | |
| 79 | 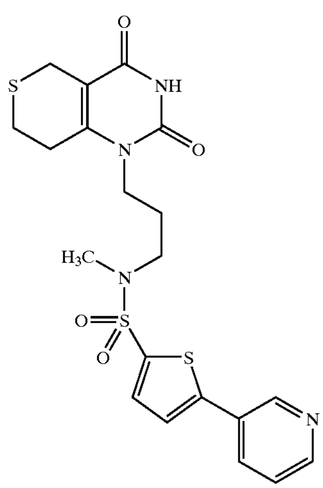 | 3.13 (C) | 479.2 | | |

-continued

| Example No. | Structure | Rt [min] [a] | MS [M + H]⁺ | Rf value [b] | m.p. [° C.] |
|---|---|---|---|---|---|
| 80 | 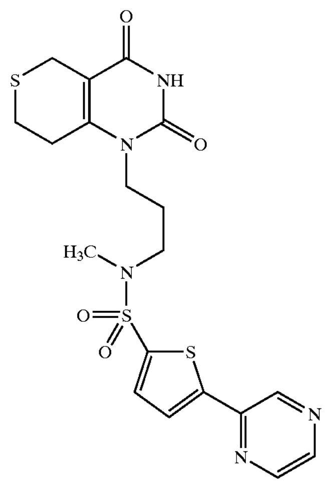 | 3.38 (C) | 480.1 | | |
| 81 | 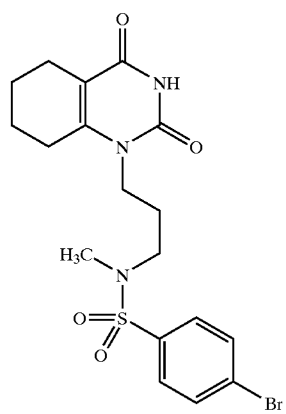 | 4.17 (A) | 473.1 [M + NH₄]⁺ | | |
| 82 | 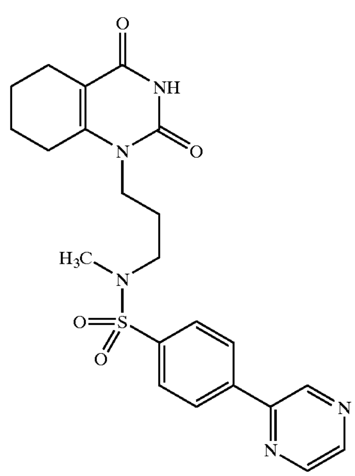 | 2.29 (C) | 473.1 [M + NH₄]⁺ | | |

-continued

| Example No. | Structure | Rt [min] [a] | MS [M + H]+ | Rf value [b] | m.p. [° C.] |
|---|---|---|---|---|---|
| 83 | 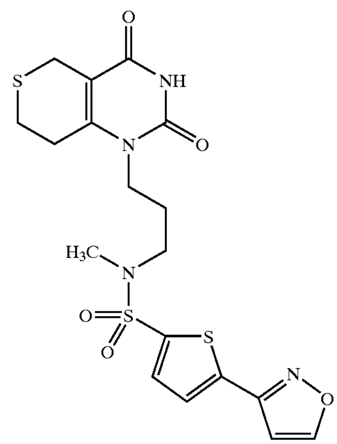 | 3.30 (C) | 469.1 | | |
| 84 | 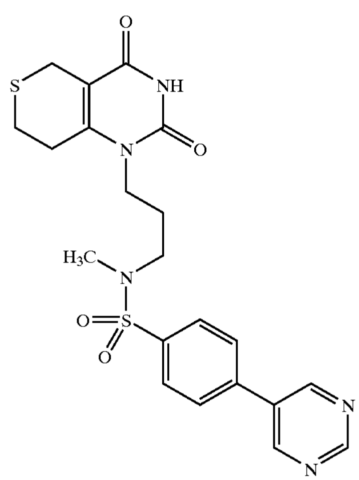 | 3.69 (C) | 474 | | |
| 85 | 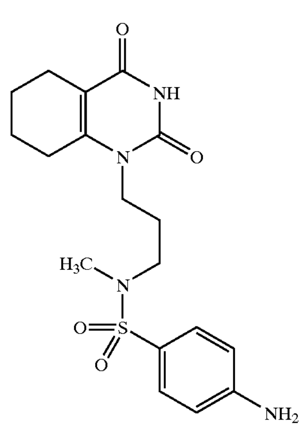 | 2.98 (C) | 393.2 | | |

-continued

| Example No. | Structure | Rt [min] [a] | MS [M + H]+ | Rf value [b] | m.p. [° C.] |
|---|---|---|---|---|---|
| 86 | 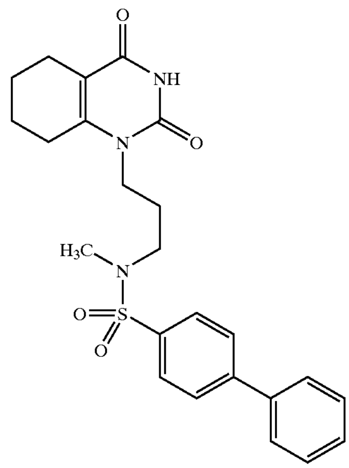 | 4.45 (A) | 454 | | |
| 87 | 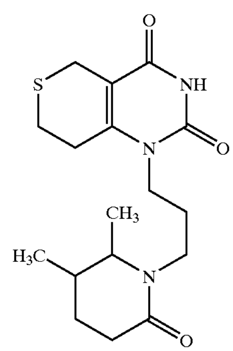 | 3.60 (C) | 352.3 | | |
| 88 | 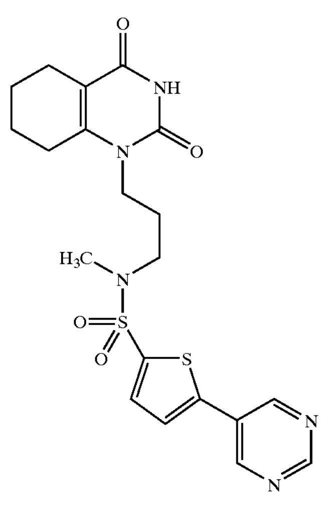 | 3.22 (C) | 462.3 | | |

-continued
| Example No. | Structure | Rt [min] [a] | MS [M + H]+ | Rf value [b] | m.p. [° C.] |
|---|---|---|---|---|---|
| 89 | 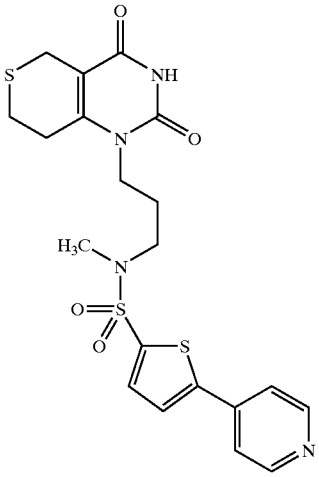 | 2.66 (C) | 77.1 [M − H]− | | |
| 90 | 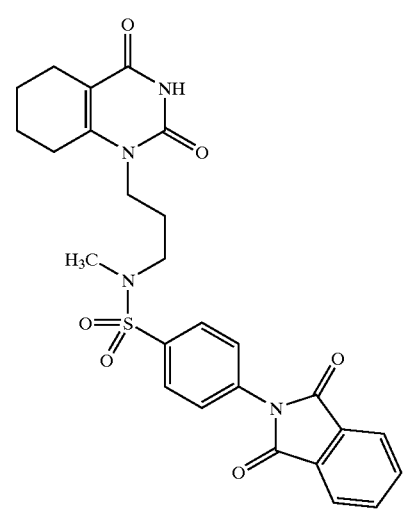 | 4.19 (A) | 523 | | |
| 91 | 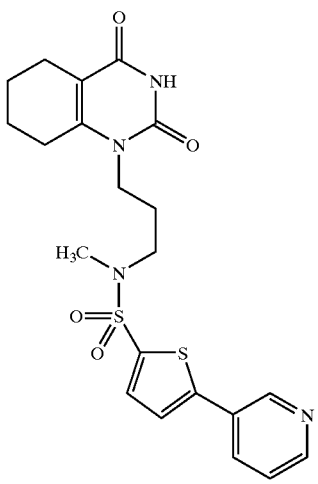 | 3.24 (C) | 461.1 | | |

-continued

| Example No. | Structure | Rt [min] [a] | MS [M + H]⁺ | Rf value [b] | m.p. [° C.] |
|---|---|---|---|---|---|
| 92 | 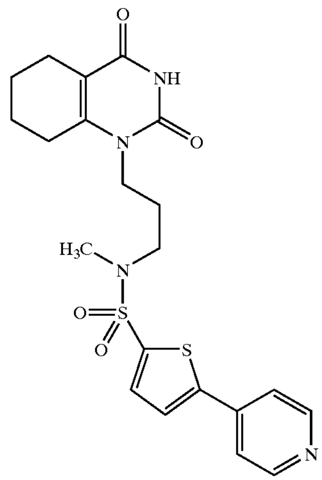 | 2.79 (C) | 461.3 | | |
| 93 | 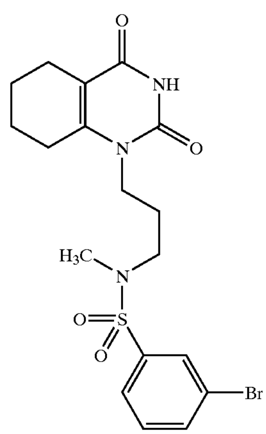 | 4.16 (A) | 473.2 [M + NH$_4$]⁺ | | |
| 94 | 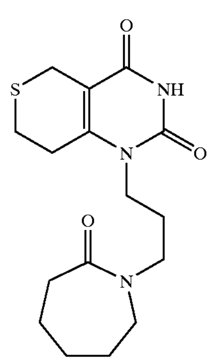 | 3.41 (C) | 338.2 | | |

-continued

| Example No. | Structure | Rt [min] [a] | MS [M + H]+ | Rf value [b] | m.p. [° C.] |
|---|---|---|---|---|---|
| 95 | 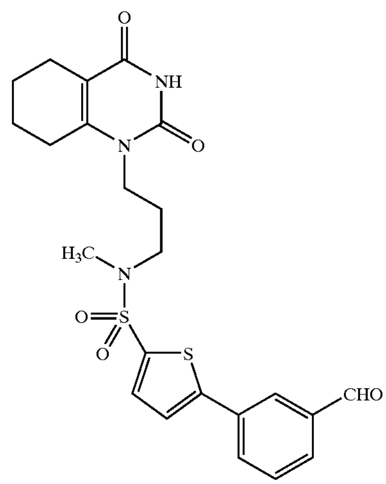 | 3.84 (C) | 488.2 | | |
| 96 | 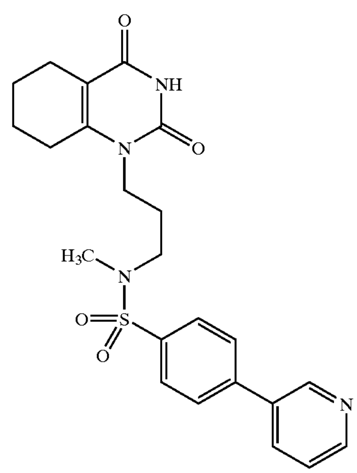 | 3.57 (A) | 455.1 | | |
| 97 | 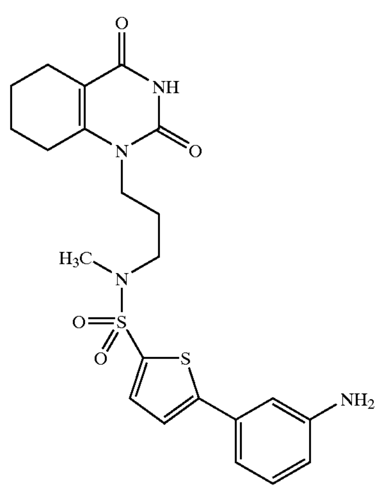 | 3.43 (C) | 475.3 | | |

-continued

| Example No. | Structure | Rt [min] [a] | MS [M + H]+ | Rf value [b] | m.p. [° C.] |
|---|---|---|---|---|---|
| 98 | 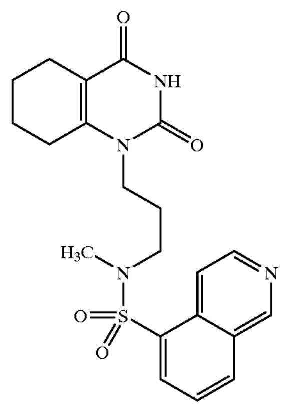 | 2.82 (C) | 429.2 | | |
| 99 | 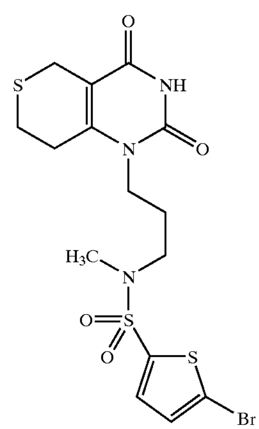 | 3.75 (C) | 480.1 | | |
| 100 | 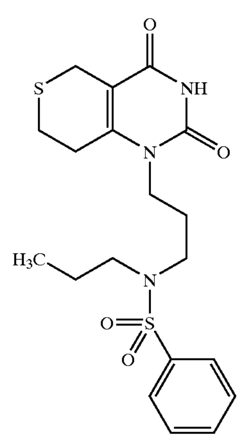 | 3.73 (C) | 406 | | |

-continued

| Example No. | Structure | Rt [min] [a] | MS [M + H]+ | Rf value [b] | m.p. [° C.] |
|---|---|---|---|---|---|
| 101 | 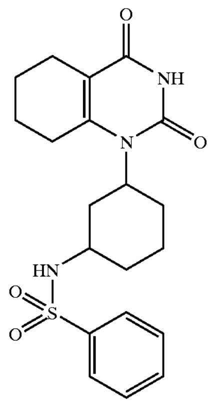 | 4.00 (C) | 404.5 | | |
| 102 | 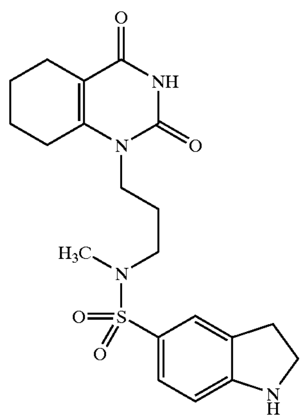 | 3.08 (C) | 419 | | |
| 103 | 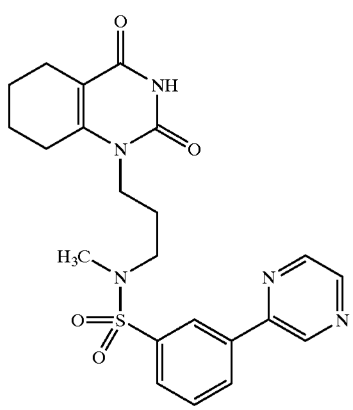 | 3.91 (A) | 456.1 | | |
| 104 | 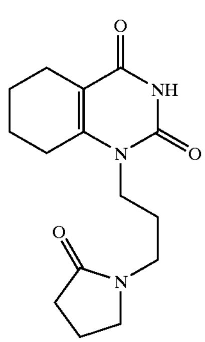 | 3.20 (C) | 292 | | |

-continued

| Example No. | Structure | Rt [min] [a] | MS [M + H]+ | Rf value [b] | m.p. [° C.] |
|---|---|---|---|---|---|
| 105 | 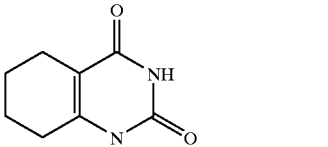 | 3.6 (A) | 455 | | |

[a] HPLC Methods (A): Mobile phase A: 0.5% $HClO_4$ in water; mobile phase B: acetonitrile; gradient: 0.5 min 98% A, 2% B; 4.5 min 10% A, 90% B; 6.7 min 98% A, 2% B; flow rate: 0.75 ml/min; UV detection at 210 nm; column: Kromasil C18 60×2 mm.

(B): Mobile phase A: 0.5% $H_3PO_4$ in water; mobile phase B: acetonitrile; gradient: 0.5 min 90% A, 10% B; 4.5 min 10% A, 90% B; 8.5 min 90% A, 10% B; flow rate: 0.75 ml/min; UV detection at 210 nm; column: Kromasil C18 60×2 mm.

(C): Mobile phase A: 0.1% formic acid in water; mobile phase B: 0.1% formic acid in acetonitrile; gradient: 0.5 min 90% A, 10% B; 4 min 10% A, 90% B; 6.1 min 90% A, 10% B; flow rate: 0.5 ml/min; UV detection at 210 nm; column: Symmetry C18 50×2.1 mm.

(D): Mobile phase A: 0.1% formic acid in water; mobile phase B: 0.1% formic acid acetonitrile; gradient: 1 min 95% A, 5% B; 5 min 10% A, 90% B; 6.1 min 95% A, 5% B; flow rate: 0.5 ml/min; UV detection at 210 nm; column: Symmetry C18 50×2.1 mm.

[b] TLC Solvent (E): Ethyl acetate/methanol 4:1.
(F): Cyclohexane/ethyl acetate 1:2.

What is claimed is:

1. A compound of the formula (I)

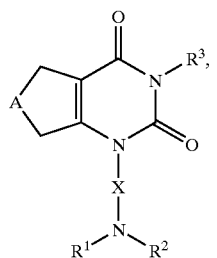

in which

A represents a ring member selected from the group consisting of:
—D—,
—$CH_2$—D—,
—D—$CH_2$—,
—CH=CH—$CH_2$—,
—$CH_2$—CH=CH—,
—$CH_2$—$CH_2$—D—,
—D—$CH_2$—$CH_2$ and
—$CH_2$—D—$CH_2$—, in which
D represents —$CH_2$—, —O— or —S—, X represents ($C_2$–$C_{10}$)-alkylene or ($C_3$–$C_8$)-cycloalkylene which are optionally mono- or polysubstituted, independently of one another, by substituents selected from the group consisting of ($C_1$–$C_6$)-alkoxy, hydroxyl, amino, mono- and di-($C_1$–$C_6$)-alkylamino and oxo, $R^1$ represents hydrogen, ($C_1$–$C_6$)-alkyl which is optionally mono- or polysubstituted by halogen, or represents ($C_3$–$C_8$)-cycloalkyl, $R^2$ represents a group of the formula —$SO_2$—$R^4$, —$SO_2$—$NR^5R^6$, —CO—$R^7$, —CO—$NR^8R^9$ or —CO—$OR^{10}$, in which $R^4$ represents ($C_1$–$C_6$)-alkyl or ($C_3$–$C_8$)-cycloalkyl which are optionally substituted by ($C_1$–$C_4$)-alkoxy, ($C_6$–$C_{10}$)-aryl, 5- to 10-membered heteroaryl having up to 4 heteroatoms from the group consisting of N, O and/or S, or up to trisubstituted by halogen, where the aryl or heteroaryl radicals for their part are optionally substituted by hydroxyl, ($C_1$–$C_4$)-alkoxy, ($C_1$–$C_4$)-alkyl, halogen, cyano or nitro, or represents a group of the formula

—G—E in which

E represents ($C_6$–$C_{10}$)-aryl or a 5- to 13-membered saturated, partially unsaturated or aromatic heterocycle having up to four heteroatoms from the group consisting of N, O and S, where the ring systems are in each case optionally substituted up to five times by identical or different substituents selected from the group consisting of nitro, cyano, halogen, optionally benzamido-substituted ($C_1$–$C_6$)-alkyl, trifluoromethyl, ($C_3$–$C_6$)-cycloalkyl, hydroxyl, oxo, ($C_1$–$C_6$)-alkoxy, carboxyl, ($C_1$–$C_6$)-alkoxycarbonyl, ($C_1$–$C_6$)-alkanoyl, amino, aminocarbonyl, mono- and di-($C_1$–$C_6$)-alkylaminocarbonyl, ($C_1$–$C_6$)-alkanoylamino, ($C_1$–$C_6$)-alkylsulphonyl, ($C_1$–$C_6$)-alkylthio, optionally ($C_1$–$C_4$)-alkyl-, halogen- or nitro-substituted phenylsulphonyl,

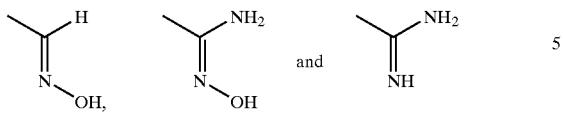

and

G is absent or represents ($C_6$–$C_{10}$)-arylene or 5- to 10-membered heteroarylene having up to 4 heteroatoms from the group consisting of N, O and S, which are in each case optionally substituted up to three times by identical or different substituents selected from the group consisting of nitro, cyano, halogen, ($C_1$–$C_6$)-alkyl, trifluoromethyl, ($C_3$–$C_6$)-cycloalkyl, hydroxyl, ($C_1$–$C_6$)-alkoxy, carboxyl, ($C_1$–$C_6$)-alkoxycarbonyl, ($C_1$–$C_6$)-alkanoyl, amino, aminocarbonyl, mono- and di-($C_1$–$C_6$)-alkylaminocarbonyl, ($C_1$–$C_6$)-alkanoylamino, ($C_1$–$C_6$)-alkylsulphonyl and ($C_1$–$C_6$)-alkylthio, $R^5$ and $R^6$ independently of one another each represent hydrogen, ($C_3$–$C_8$)-cycloalkyl, ($C_1$–$C_6$)-alkyl, ($C_6$–$C_{10}$)-aryl or 5- to 10-membered heteroaryl which, independently of one another, are in each case optionally substituted by ($C_1$–$C_4$)-alkoxy, hydroxyl, cyano, carboxyl, ($C_1$–$C_4$)-alkoxycarbonyl, up to three times by halogen, by ($C_6$–$C_{10}$)-aryl or by 5- to 10-membered heteroaryl, where the aryl and hetaryl radicals for their part are optionally substituted by hydroxyl, ($C_1$–$C_4$)-alkoxy, ($C_1$–$C_4$)-alkyl, halogen, cyano or nitro, or $R^5$ and $R^6$ together with the nitrogen atom to which they are attached form a saturated 3- to 7-membered heterocycle in which optionally one carbon ring member is replaced by a further heteroatom from the group consisting of nitrogen, oxygen and sulphur and which is optionally substituted by ($C_1$–$C_4$)-alkyl, hydroxyl, ($C_1$–$C_4$)-alkoxy, oxo, carboxyl or ($C_1$–$C_4$)-alkoxycarbonyl, $R^7$ represents ($C_1$–$C_6$)-alkyl or ($C_3$–$C_8$)-cycloalkyl which are optionally substituted by ($C_1$–$C_4$)-alkoxy, ($C_6$–$C_{10}$)-aryl, 5- to 10-membered heteroaryl having up to 4 heteroatoms from the group consisting of N, O and S or up to three times by halogen, where the aryl or heteroaryl radicals for their part are optionally substituted by hydroxyl, ($C_1$–$C_4$)-alkoxy, ($C_1$–$C_4$)-alkyl, halogen, cyano or nitro, or represents a group of the formula

—G—E in which

E represents ($C_6$–$C_{10}$)-aryl or a 5- to 13-membered saturated, partially unsaturated or aromatic heterocycle having up to four heteroatoms from the group consisting of N, O and S, where the ring systems are in each case optionally substituted up to five times by identical or different substituents selected from the group consisting of nitro, cyano, halogen, optionally benzamido-substituted ($C_1$–$C_6$)-alkyl, trifluoromethyl, ($C_3$–$C_6$)-cycloalkyl, hydroxyl, oxo, ($C_1$–$C_6$)-alkoxy, carboxyl, ($C_1$–$C_6$)-alkoxycarbonyl, ($C_1$–$C_6$)-alkanoyl, amino, aminocarbonyl, mono- and di-($C_1$–$C_6$)-alkylaminocarbonyl, ($C_1$–$C_6$)-alkanoylamino, ($C_1$–$C_6$)-alkylsulphonyl, ($C_1$–$C_6$)-alkylthio and optionally ($C_1$–$C_4$)-alkyl-, halogen- or nitro-substituted phenylsulphonyl, and G is absent or represents ($C_6$–$C_{10}$)-arylene or 5- to 10-membered heteroarylene having up to 4 heteroatoms from the group consisting of N, O and S, which are in each case optionally substituted up to three times by identical or different substituents selected from the group consisting of nitro, cyano, halogen, ($C_1$–$C_6$)-alkyl, trifluoromethyl, ($C_3$–$C_6$)-cycloalkyl, hydroxyl, ($C_1$–$C_6$)-alkoxy, carboxyl, ($C_1$–$C_6$)-alkoxycarbonyl, ($C_1$–$C_6$)-alkanoyl, amino, aminocarbonyl, mono- and di-($C_1$–$C_6$)-alkylaminocarbonyl, ($C_1$–$C_6$)-alkanoylamino, ($C_1$–$C_6$)-alkylsulphonyl and ($C_1$–$C_6$)-alkylthio, $R^8$ and $R^9$ independently of one another each represent hydrogen, ($C_3$–$C_8$)-cycloalkyl or ($C_1$–$C_6$)-alkyl which are in each case optionally substituted by ($C_1$–$C_4$)-alkoxy, hydroxyl, cyano, carboxyl, ($C_1$–$C_4$)-alkoxycarbonyl, up to three times by halogen, by ($C_6$–$C_{10}$)-aryl or by 5- to 10-membered heteroaryl, where the aryl and hetaryl radicals for their part are optionally substituted by hydroxyl, ($C_1$–$C_4$)-alkoxy, ($C_1$–$C_4$)-alkyl, halogen, cyano or nitro, or $R^8$ and $R^9$ together with the nitrogen atom to which they are attached form a saturated 3- to 7-membered heterocycle in which optionally one carbon ring member is replaced by a further heteroatom from the group consisting of nitrogen, oxygen and sulphur and which is optionally substituted by ($C_1$–$C_4$)-alkyl, hydroxyl, ($C_1$–$C_4$)-alkoxy, oxo, carboxyl or ($C_1$–$C_4$)-alkoxycarbonyl, $R^{10}$ represents ($C_1$–$C_6$)-alkyl, ($C_3$–$C_8$)-cycloalkyl or ($C_6$–$C_{10}$)-aryl which are optionally mono- or polysubstituted by hydroxyl, ($C_1$–$C_4$)-alkoxy, halogen, cyano or nitro, or $R^1$ and $R^2$ together with the nitrogen atom to which they are attached form a saturated 5- to 10-membered mono- or bicyclic heterocycle, which has a carbonyl or sulphonyl group directly adjacent to the nitrogen atom to which $R^1$ and $R^2$ are attached, in which optionally up to two carbon ring members are replaced by oxygen and/or sulphur and which is optionally substituted up to three times by identical or different substituents selected from the group consisting of ($C_1$–$C_6$)-alkyl, hydroxyl, oxo, ($C_1$–$C_6$)-alkoxy, carboxyl, ($C_1$–$C_4$)-alkoxycarbonyl and halogen, and $R^3$ represents hydrogen or ($C_1$–$C_6$)-alkoxycarbonyl or a pharmaceutically acceptable salt or hydrate thereof.

2. A compound according to claim 1, in which

A represents a ring member —$CH_2$—D— or —D—$CH_2$—, in which

D represents —$CH_2$—, —O— or —S—,

X represents ($C_2$–$C_4$)-alkylene or cyclohexylene, $R^1$ represents hydrogen, ($C_1$–$C_4$)-alkyl which is optionally substituted up to three times by fluorine, or ($C_3$–$C_6$)-cycloalkyl, $R^2$ represents a group of the formula —$SO_2$—$R^4$, —CO—$R^7$ or —CO—$OR^{10}$, in which $R^4$ represents ($C_1$–$C_4$)-alkyl which is optionally substituted up to three times by fluorine, or represents a group of the formula

—G—E in which
E represents $(C_6-C^{10})$-aryl or a 5- to 13-membered saturated, partially unsaturated or aromatic heterocycle having up to three heteroatoms from the group consisting of N, O and S, where the ring systems are in each case optionally substituted up to three times by identical or different substituents selected from the group consisting of nitro, cyano, fluorine, chlorine, bromine, optionally benzamido-substituted $(C_1-C_4)$-alkyl, trifluoromethyl, $(C_3-C_6)$-cycloalkyl, hydroxyl, oxo, $(C_1-C_4)$-alkoxy, carboxyl, $(C_1-C_4)$-alkoxycarbonyl, $(C_1-C_4)$-alkanoyl, amino, aminocarbonyl, mono- and di-$(C_1-C_4)$-alkylaminocarbonyl, $(C_1-C_4)$-alkanoylamino, $(C_1-C_4)$-alkylsulphonyl, $(C_1-C_4)$-alkylthio and optionally methyl-, fluorine-, chlorine-, bromine- or nitro-substituted phenylsulphonyl, and 'G is absent or represents $(C_6-C_{10})$-arylene or 5-or 6-membered heteroarylene having up to three heteroatoms from the group consisting of N, O and S, which are in each case optionally substituted up to three times by identical or different substituents selected from the group consisting of nitro, cyano, fluorine, chlorine, bromine, $(C_1-C_4)$-alkyl, trifluoromethyl, $(C_3-C_6)$-cycloalkyl, hydroxyl, $(C_1-C_4)$-alkoxy, carboxyl, $(C_1-C_4)$-alkoxycarbonyl, $(C_1-C_4)$-alkanoyl, amino, aminocarbonyl, mono- and di-$(C_1-C_4)$-alkylaminocarbonyl, $(C_1-C_4)$-alkanoyl amino, $(C_1-C_4)$-alkylsulphonyl and $(C_1-C_4)$-alkylthio, $R^7$ represents $(C_6-C_{10})$-aryl which is optionally substituted by nitro, $R^{10}$ represents $(C_1-C_4)$-alkyl which is optionally substituted up to three times by chlorine, or $R^1$ and $R^2$ together with the nitrogen atom to which they are attached form a saturated 5- to 10-membered mono- or bicyclic heterocycle which has a carbonyl group directly adjacent to the nitrogen atom to which $R^1$ and $R^2$ are attached, in which optionally up to two carbon ring members are replaced by oxygen and/or sulphur and which is optionally substituted up to three times by identical or different substituents selected from the group consisting of $(C_1-C_4)$-alkyl, hydroxyl, oxo, $(C_1-C_4)$-alkoxy, carboxyl, $(C_1-C_4)$-alkoxycarbonyl and halogen, and $R^3$ represents hydrogen or a pharmaceutically acceptable salt or hydrate thereof.

3. A compound according to claim 1, in which

A represents a ring member —CH$_2$—D— or —D—CH$_2$—, in which

D represents —CH$_2$—, —O— or —S—,

X represents $(C_2-C_4)$-alkylene, $R^1$ represents hydrogen, $(C_1-C_4)$-alkyl which is optionally substituted up to three times by fluorine, or $(C_3-C_6)$-cycloalkyl, $R^2$ represents a group of the formula

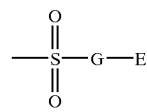

in which

E represents $(C_6-C_{10})$-aryl or a 5- to 13-membered saturated, partially unsaturated or aromatic heterocycle having up to three heteroatoms from the group consisting of N, O and S, where the ring systems are in each case optionally substituted up to three times by identical or different substituents selected from the group consisting of nitro, cyano, fluorine, chlorine, bromine, optionally benzamido-substituted $(C_1-C_4)$-alkyl, trifluoromethyl, $(C_3-C_6)$-cycloalkyl, hydroxyl, oxo, $(C_1-C_4)$-alkoxy, carboxyl, $(C_1-C_4)$-alkoxycarbonyl, $(C_1-C_4)$-alkanoyl, amino, aminocarbonyl, mono- and di-$(C_1-C_4)$-alkylaminocarbonyl, $(C_1-C_4)$-alkanoylamino, $(C_1-C_4)$-alkylsulphonyl, $(C_1-C_4)$-alkylthio and optionally methyl-, fluorine-, chlorine-, bromine- or nitro-substituted phenylsulphonyl, and G is absent or represents $(C_6-C_{10})$-arylene or 5- or 6-membered heteroarylene having up to three heteroatoms from the group consisting of N, O and S, which are in each case optionally substituted up to three times by identical or different substituents selected from the group consisting of nitro, cyano, fluorine, chlorine, bromine, $(C_1-C_4)$-alkyl, trifluoromethyl, $(C_3-C_6)$-cycloalkyl, hydroxyl, $(C_1-C_4)$-alkoxy, carboxyl, $(C_1-C_4)$-alkoxycarbonyl, $(C_1-C_4)$-alkanoyl, amino, aminocarbonyl, mono- and di-$(C_1-C_4)$-alkylaminocarbonyl, $(C_1-C_4)$-alkanoylamino, $(C_1-C_4)$-alkylsulphonyl and $(C_1-C_4)$-alkylthio, or $R^1$ and $R^2$ together with the nitrogen atom to which they are attached form a saturated 5- to 10-membered mono- or bicyclic heterocycle which has a carbonyl group directly adjacent to the nitrogen atom to which $R^1$ and $R^2$ are attached, in which optionally up to two carbon ring members are replaced by oxygen and/or sulphur and which is optionally substituted up to three times by identical or different substituents selected from the group consisting of $(C_1-C_4)$-alkyl, hydroxyl, oxo, $(C_1-C_4)$-alkoxy, carboxyl, $(C_1-C_4)$-alkoxycarbonyl and halogen, and $R^3$ represents hydrogen or a pharmaceutically acceptable salt or hydrate thereof.

4. A compound according to claim 1, in which

A represents a ring member —CH$_2$—D— or —D—CH$_2$—, in which

D represents —CH$_2$— or —S—,

X represents $(C_2-C_4)$-alkylene, $R^1$ represents hydrogen, methyl, trifluoromethyl or cyclopropyl, $R^2$ represents a group of the formula

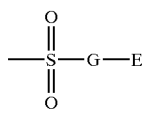

in which

E represents $(C_6-C_{10})$-aryl or a 5- to 10-membered partially unsaturated or aromatic heterocycle having up to three heteroatoms from the group consisting of N, O and S, where the ring systems are in each case optionally substituted up to two times by identical or different substituents selected from the group consisting of nitro, cyano, amino, fluorine, chlorine, bromine, $(C_1-C_4)$-alkyl, trifluoromethyl, $(C_3-C_6)$-cycloalkyl, hydroxyl, oxo and $(C_1-C_4)$-alkoxy, and G is absent or represents phenylene or thienylene, and $R^3$ represents hydrogen,
or a pharmaceutically acceptable salt or hydrate thereof.
5. A compound as recited in claim 1 selected from the group consisting of
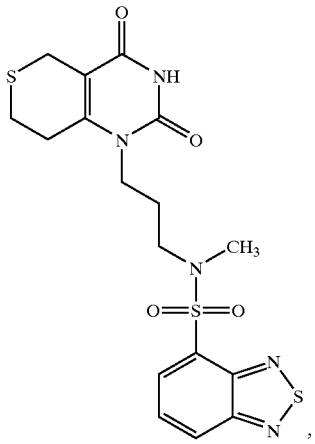
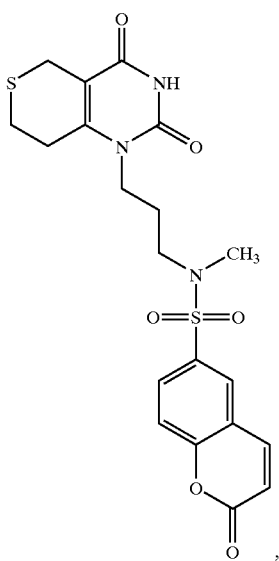
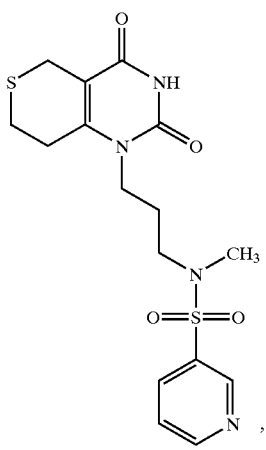
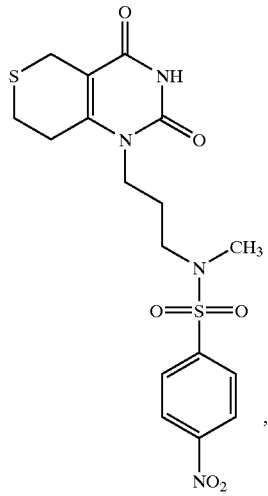
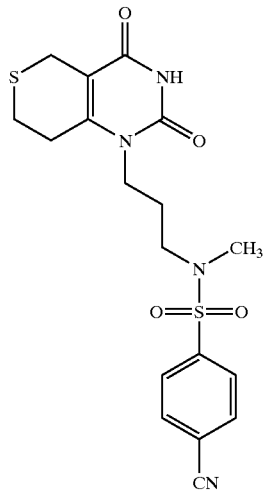
and
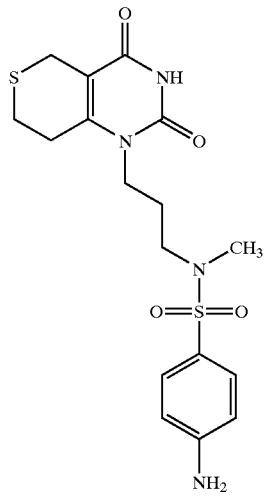
or a pharmaceutically acceptable salt or hydrate thereof.
6. A process for preparing compounds of the formula (I), as defined in claim 1, characterized in that compounds of the formula (IV)

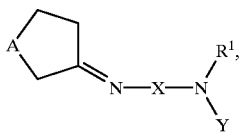

(IV)

in which
Y represents $R^2$ or a customary amino protective group and A, X, $R^1$ and $R^2$ are each as defined in claim 1 are reacted with chlorocarbonyl isocyanate to give compounds of the formula (V)

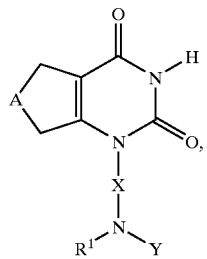

(V)

in which
Y represents $R^2$ or a customary amino protective group and A, X, $R^1$ and $R^2$ are each as defined in claim 1,
if Y represents a customary amino protective group, compounds of the formula (V) are, if appropriate, converted, by removal of this protective group, into compounds of the formula (VI)

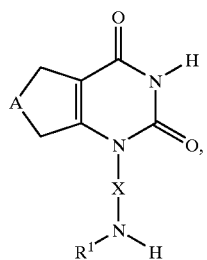

(VI)

in which

A, X and $R^1$ are each as defined in claim 1 and are reacted with compounds of the formula (VII)

$$R^2\text{—T} \qquad \text{(VII)}$$

in which
$R^2$ is as defined in claim 1 and T represents a leaving group to give compounds of the formula (V) in which
Y represents $R^2$ and A, X, $R^1$ and $R^2$ are each as defined in claim 1 and, if appropriate, compounds of the formula (V) are reacted with compounds of the formula (VIII)

$$R^3\text{—T} \qquad \text{(VIII)}$$

in which
$R^3$ is as defined in claim 1, but not hydrogen, and T represents a leaving group to give compounds of the formula (I) in which $R^3$ is as defined in claim 1, but not hydrogen.

7. A composition comprising at least one compound of the formula (I), as defined in claim 1, and at least one further active compound.

8. A composition comprising at least one compound of the formula (I), as defined in claim 1, and at least one further auxiliary.

9. A method of treating or preventing PARS-mediated ischaemic and reperfusion damage, or of treating PARS-mediated traumatic brain injuries, arthritis, type II diabetes, chronic colitis, inflammatory pulmonary disorders, or acute myocardial infarction, comprising administering to a mammal an effective amount of a PARS inhibitor of the formula (I), as defined in claim 1.

10. The method of claim 9, wherein ischaemia and reperfusion damage are prevented or treated.

11. The method of claim 10, wherein ischaemia and reperfusion damage in the heart, in the brain, or in skeletal muscle are prevented or treated.

* * * * *